(12) United States Patent
Jin et al.

(10) Patent No.: US 11,753,614 B2
(45) Date of Patent: Sep. 12, 2023

(54) **VIOLAXANTHIN-OVERPRODUCING STRAIN OF *CHLORELLA VULGARIS* AND THE METHOD FOR PRODUCING VIOLAXANTHIN USING THE SAME**

(71) Applicant: IUCF-HYU (INDUSTRY-UNIVERSITY COOPERATION FOUNDATION HANYANG UNIVERSITY), Seoul (KR)

(72) Inventors: Eon Seon Jin, Seoul (KR); Jongrae Kim, Sejong-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 178 days.

(21) Appl. No.: 17/165,192

(22) Filed: Feb. 2, 2021

(65) Prior Publication Data

US 2021/0246414 A1    Aug. 12, 2021

(30) Foreign Application Priority Data

Feb. 6, 2020    (KR) .................. 10-2020-0014252

(51) Int. Cl.
    *A61K 36/05*        (2006.01)
    *A61K 8/9722*       (2017.01)
    (Continued)

(52) U.S. Cl.
    CPC ............ *C12N 1/12* (2013.01); *A23L 17/60* (2016.08); *A23L 33/10* (2016.08); *A61K 8/9722* (2017.08);
    (Continued)

(58) Field of Classification Search
    CPC .......... C12N 1/12; C12N 9/90; A61K 8/9722; A61K 36/05; C12P 23/00;
    (Continued)

(56) References Cited

U.S. PATENT DOCUMENTS

2005/0070477 A1* 3/2005 Cochrane .................. A61P 9/12
                                                        514/1.5

FOREIGN PATENT DOCUMENTS

KR    10-2012-0137086 A    12/2012

OTHER PUBLICATIONS

Jongrae Kim, et al., "Production of natural violaxanthin from lutein deficient Chlorella vulgaris mutant generated by chemical random mutagenesis", 2019 Annual Meeting of the Korean Society of Phycology, Oct. 24-25, 2019, 2 pages.
(Continued)

*Primary Examiner* — David W Berke-Schlessel
*Assistant Examiner* — Trent R Clarke
(74) *Attorney, Agent, or Firm* — Sughrue Mion, PLLC

(57) ABSTRACT

The present invention relates to a novel violaxanthin-overproducing strain of *Chlorella vulgaris* and a method of producing violaxanthin therefrom. The inventors have developed a strain that produces violaxanthin at a significantly higher level than a wild-type strain by inducing a random chemical mutation in a *Chlorella vulgaris* strain to, and then as a result of analysis, confirmed that the strain produces violaxanthin up to 0.41% based on dry weight, which reaches the highest level that is possible to be produced in microalgae. Furthermore, as a method of effectively extracting a carotenoid pigment containing violaxanthin from the strain was established, since the strain and the developed pigment extraction method according to the present invention allow effective production and separation of violaxanthin, the strain is expected to increase commercial
(Continued)

applications such as cosmetics, health functional foods and feed.

11 Claims, 16 Drawing Sheets

Specification includes a Sequence Listing.

(51) Int. Cl.
    *C12N 1/12*     (2006.01)
    *C12N 9/90*     (2006.01)
    *C12P 23/00*     (2006.01)
    *A23L 33/10*     (2016.01)
    *A23L 17/60*     (2016.01)
    *A61Q 19/08*     (2006.01)

(52) U.S. Cl.
    CPC .............. *A61K 36/05* (2013.01); *A61Q 19/08* (2013.01); *C12N 9/90* (2013.01); *C12P 23/00* (2013.01); *C12Y 505/01018* (2013.01); *A23V 2002/00* (2013.01)

(58) Field of Classification Search
    CPC .. C12Y 505/01018; A23L 17/60; A23L 33/10; A61Q 19/08; A23V 2002/00
    See application file for complete search history.

(56)             References Cited

OTHER PUBLICATIONS

Michiko Araki, et al., "Production of Auroxanthins from Violaxanthin and 9-cis-Violaxanthin by Acidic Treatment and the Antioxidant Activities of Violaxanthin, 9-cis-Violaxanthin, and Auroxanthins", Journal of Agricultural and Food Chemistry, American Chemical Society, Dec. 14, 2016, 4 pages, vol. 64, No. 49.

Ok Ju Kim, et al., "Characterization of Chlorella Vulgaris Mutants Generated by EMS (Ethyl Methane Sulphonate)", Appl. Chem. Eng., Jun. 2015, pp. 265-269, vol. 26, No. 3.

Eiji Ishikawa, et al., "Isolation and characterization of a Chlorella mutant producing high amounts of chlorophyll and carotenoids", Journal of Applied Phycology, Oct. 2004, vol. 16, Issue 5.

Jongrae Kim, et al., "Development of a Chlorella vulgaris mutant by chemical mutagenesis as a producer for natural violaxanthin", Algal Research, 2020, pp. 1-7, vol. 46, No. 101790.

* cited by examiner

[Fig. 1B]
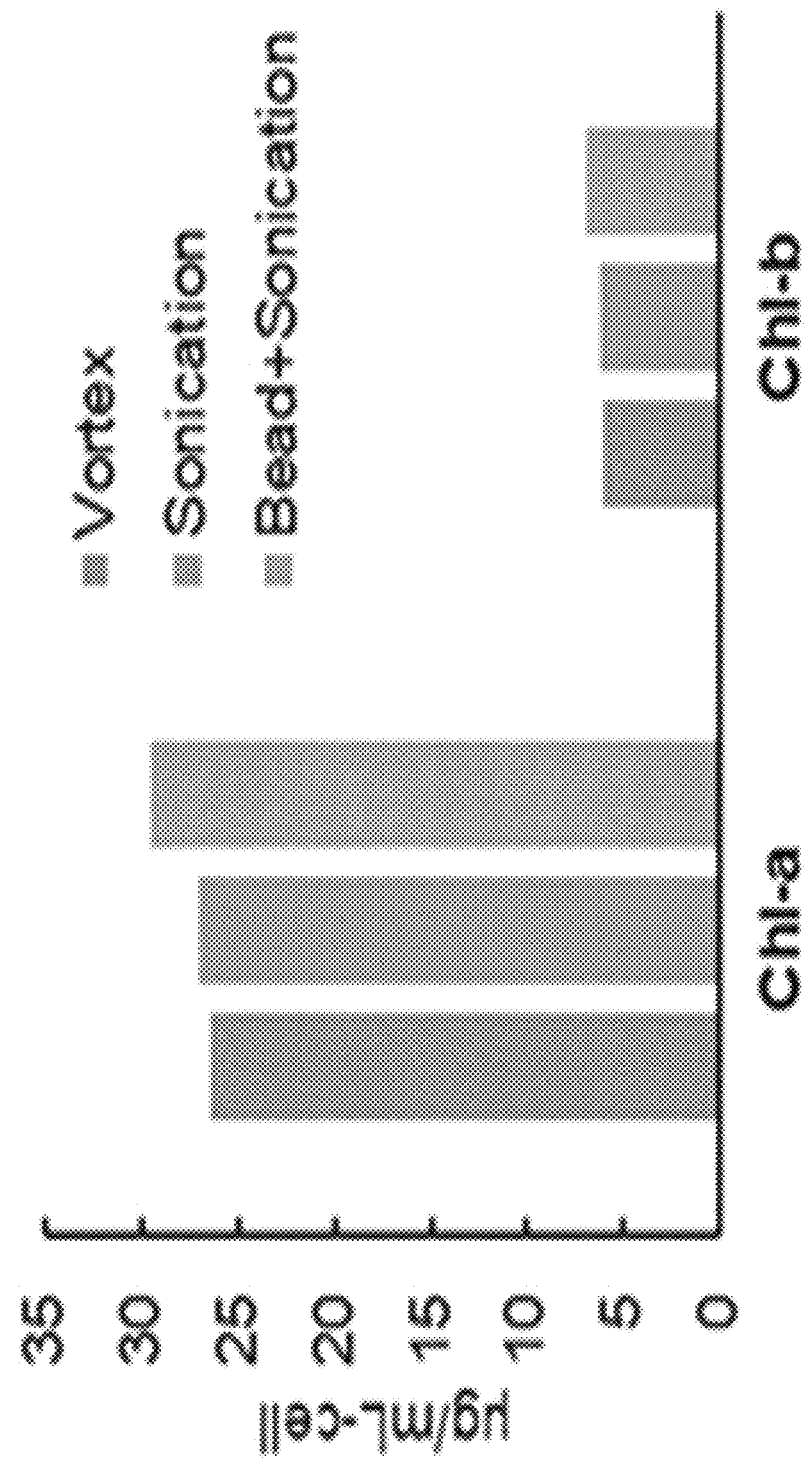

[Fig. 2A]
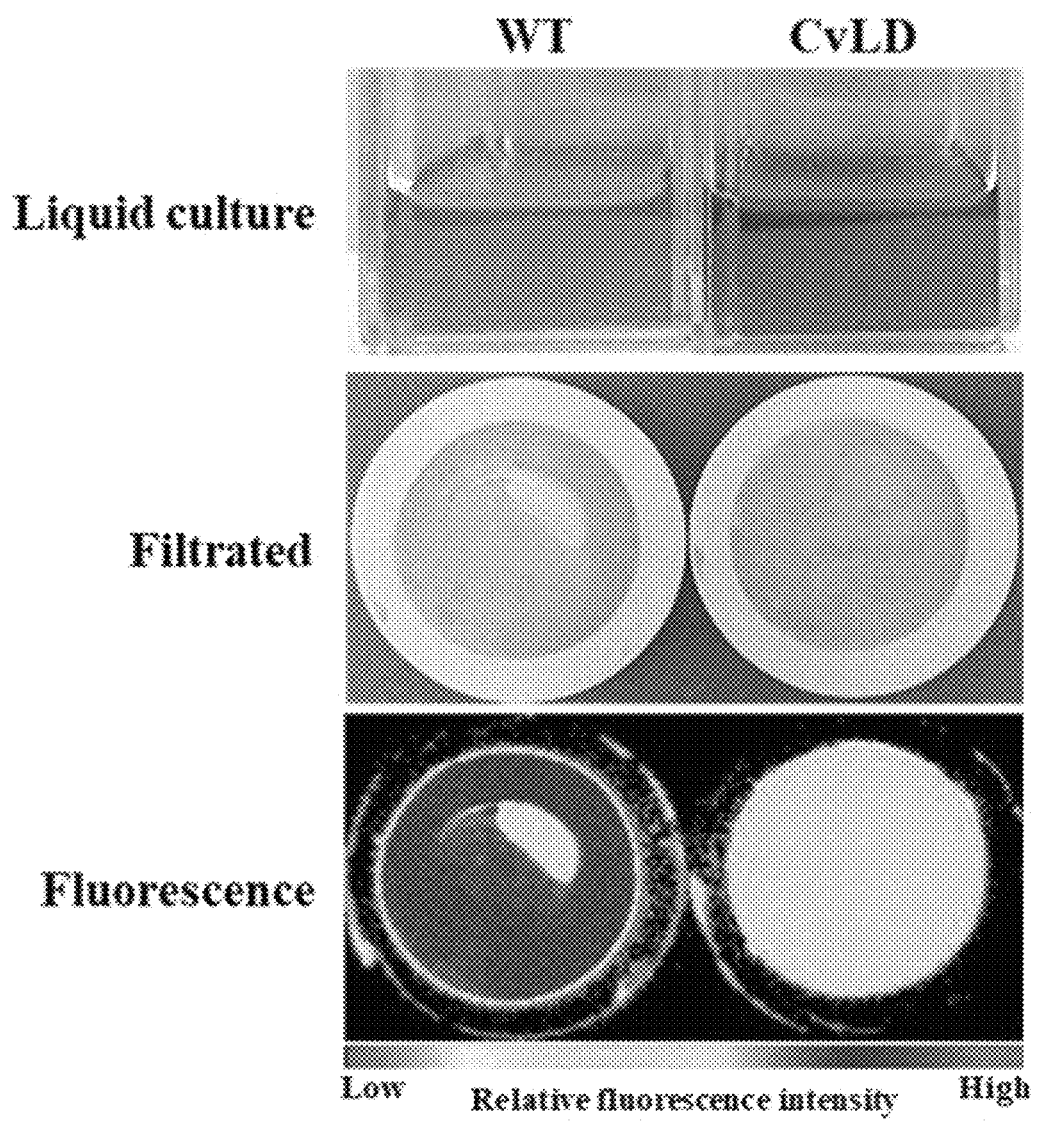

[Fig. 2B]
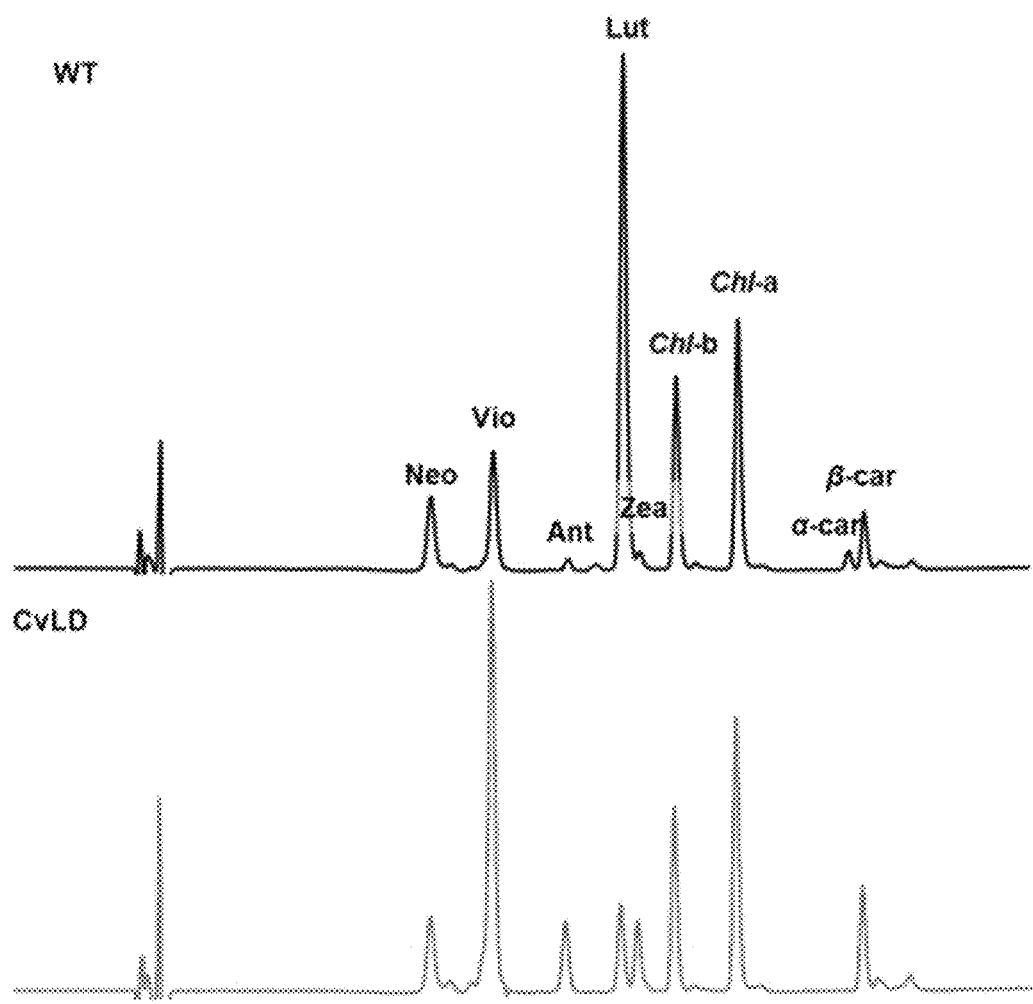

[Fig. 3A]
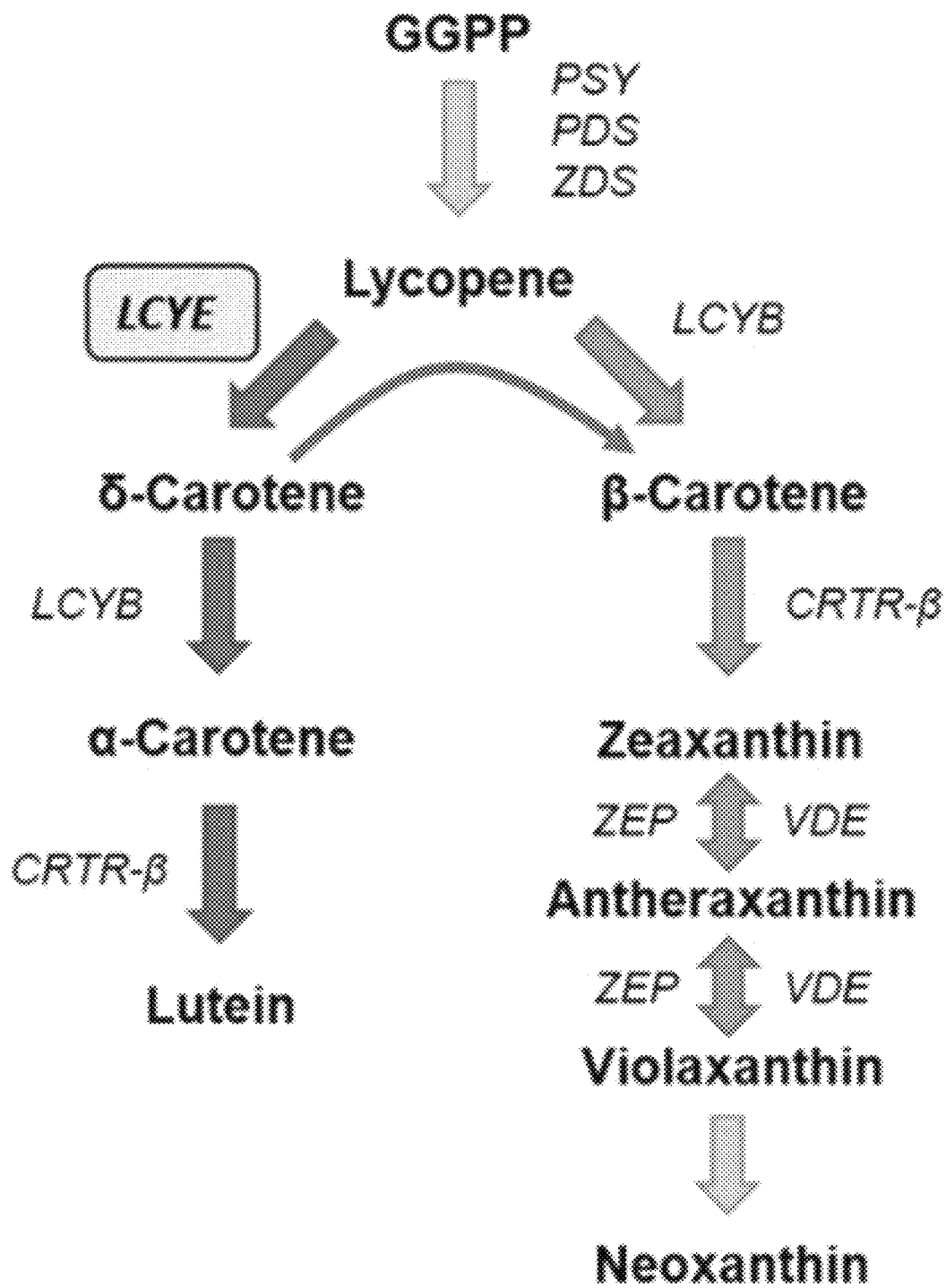

[FIG. 3B]

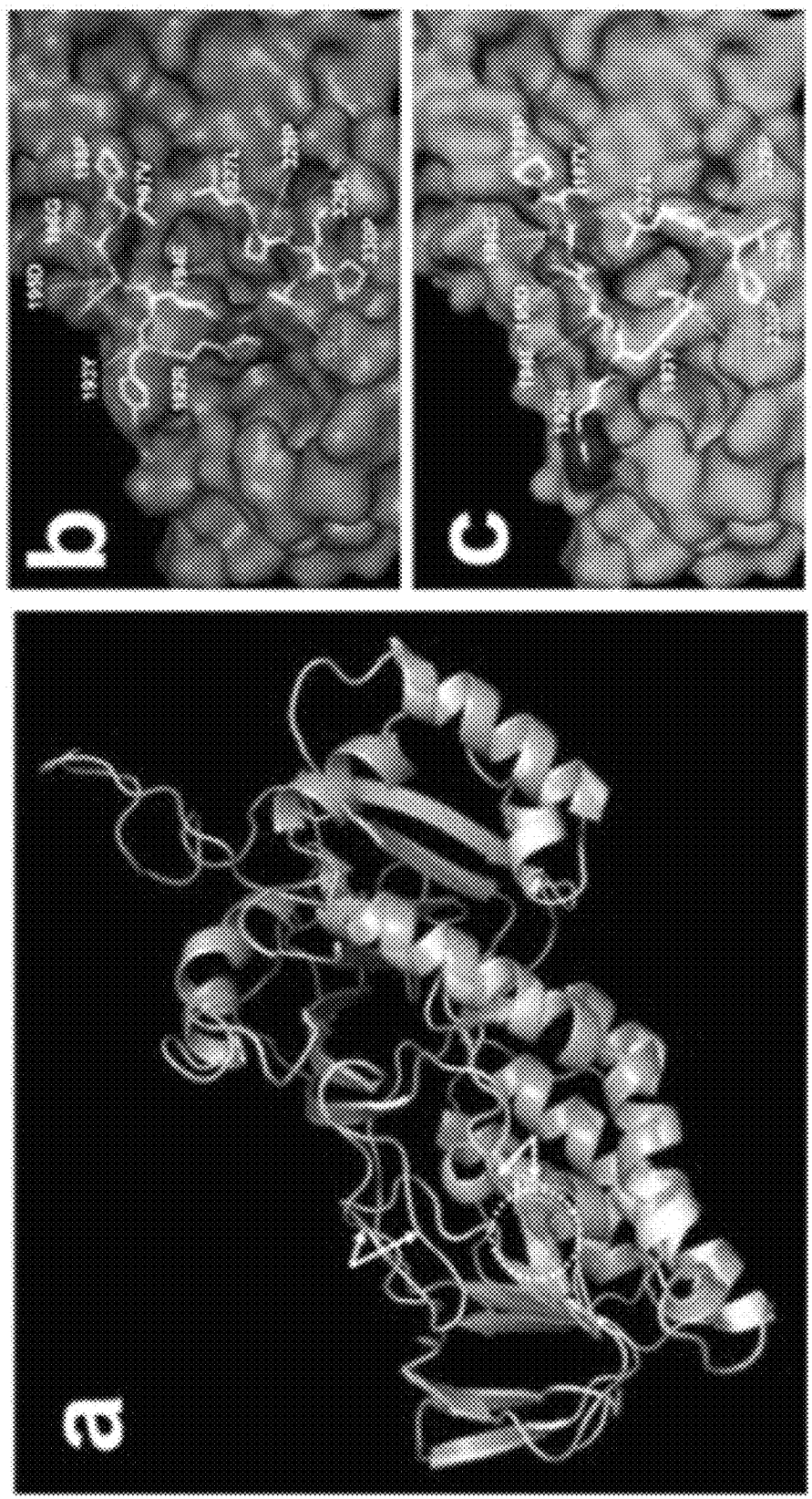
[Fig. 3C]

[Fig. 3D]
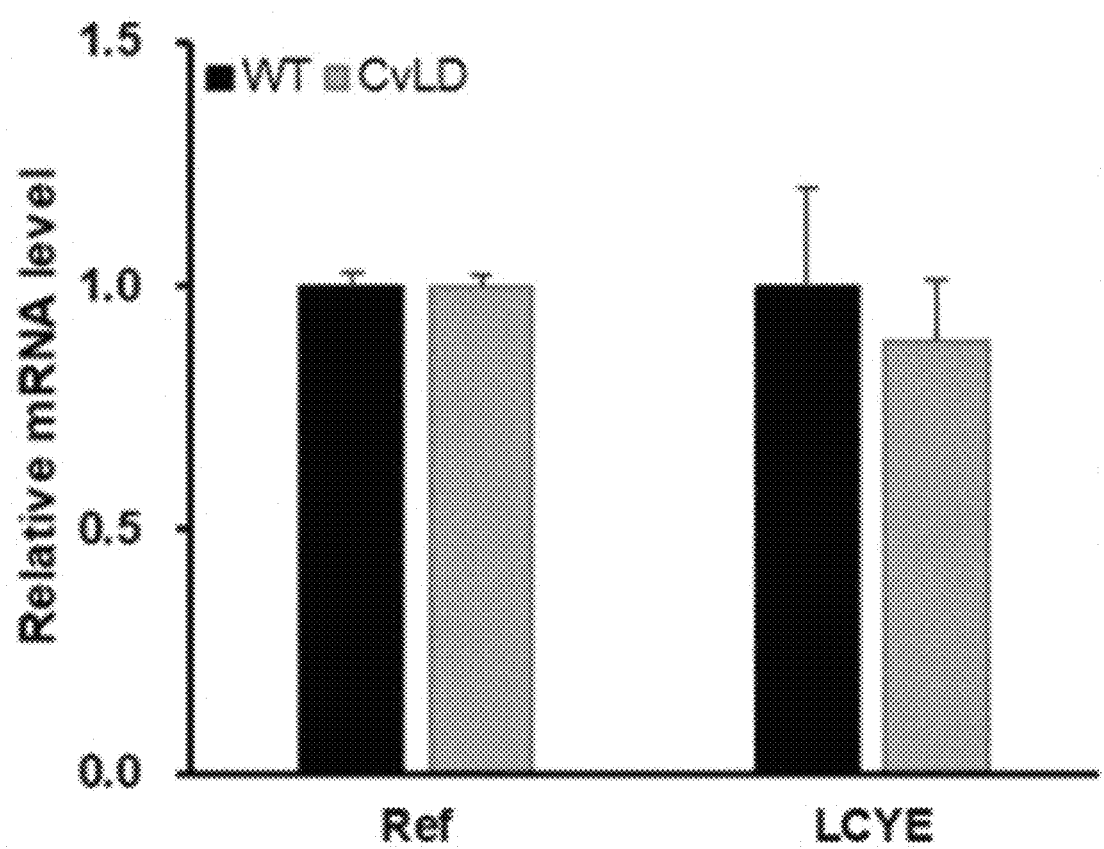

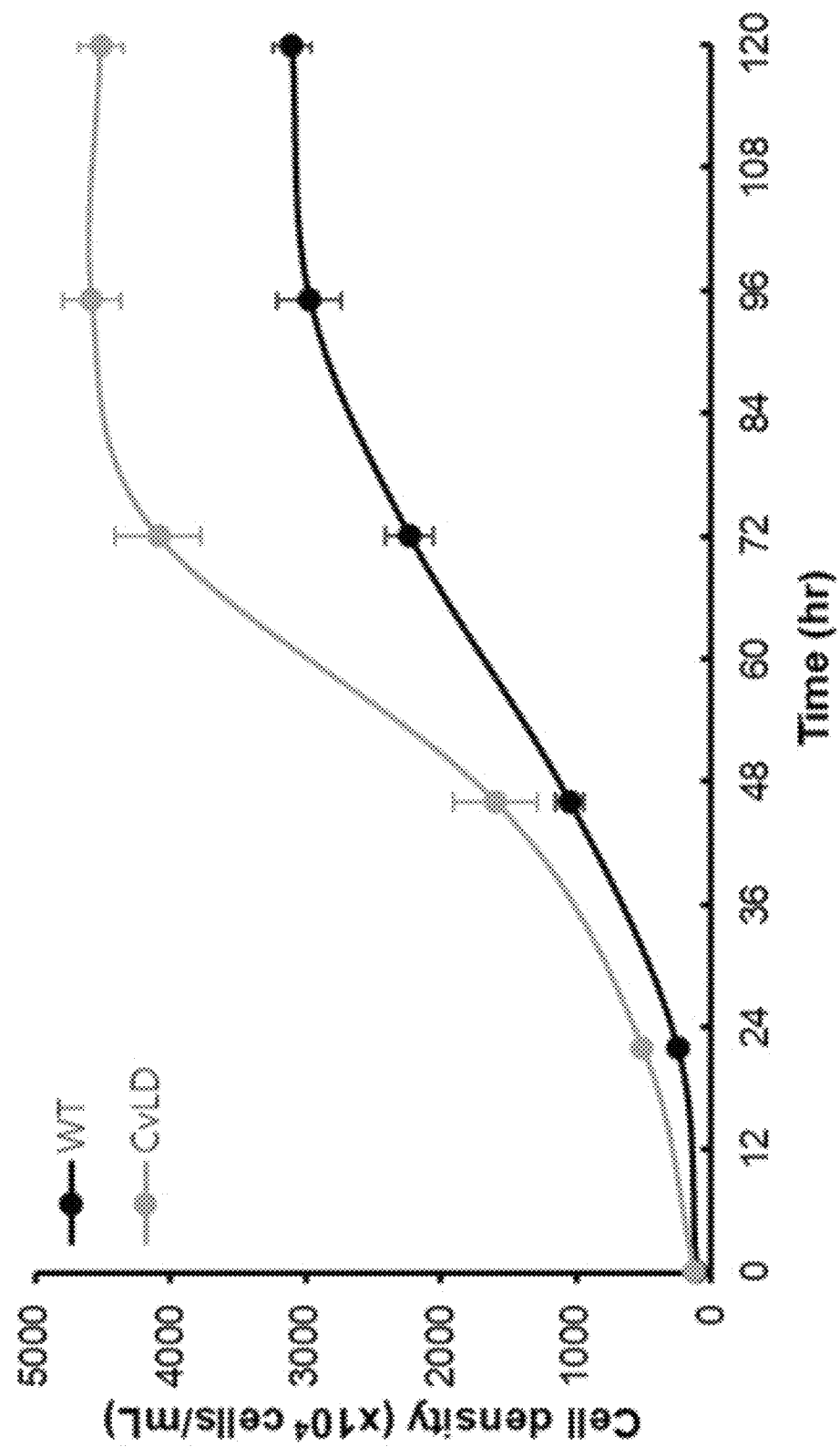
[Fig. 4A]

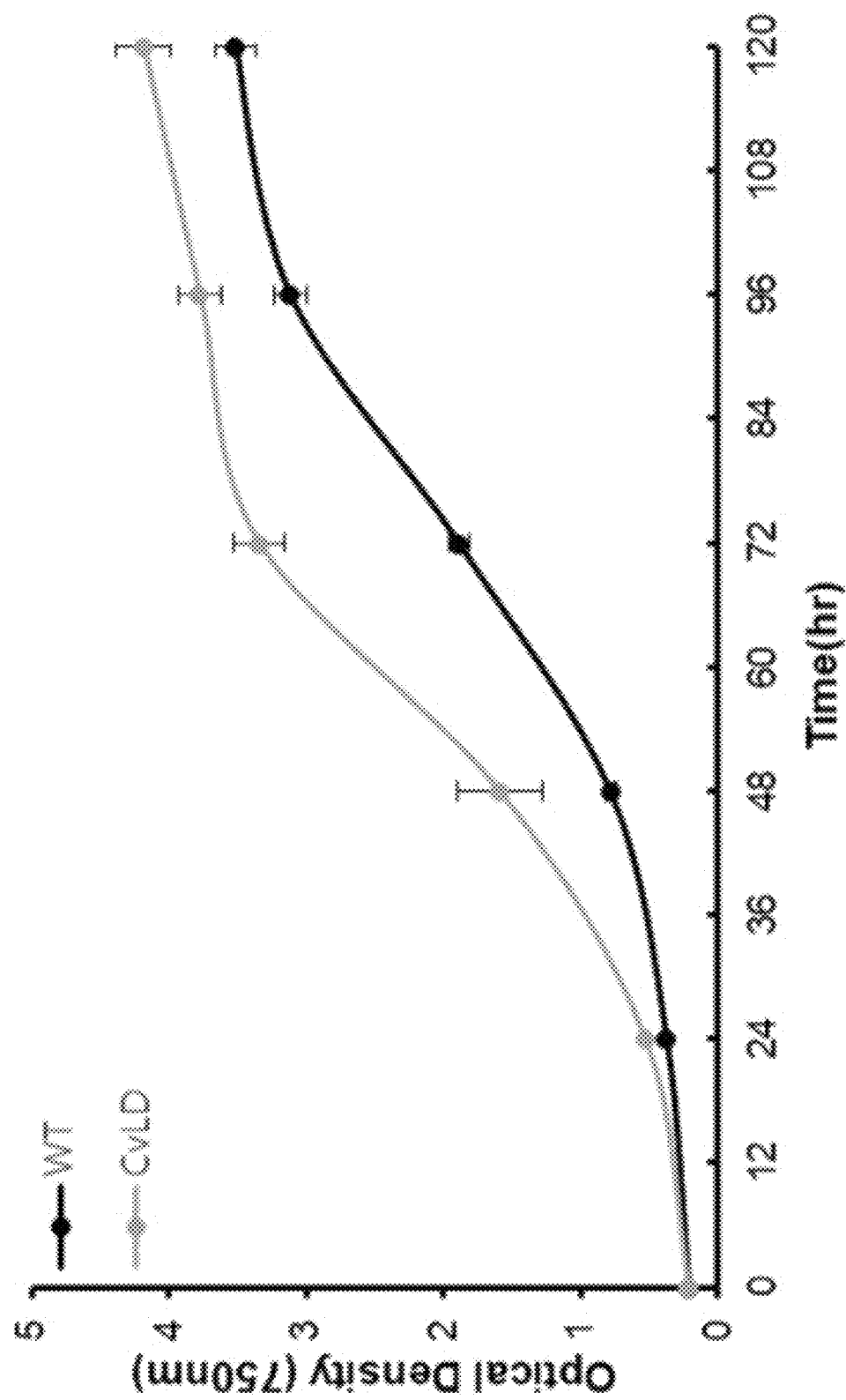
[Fig. 4B]

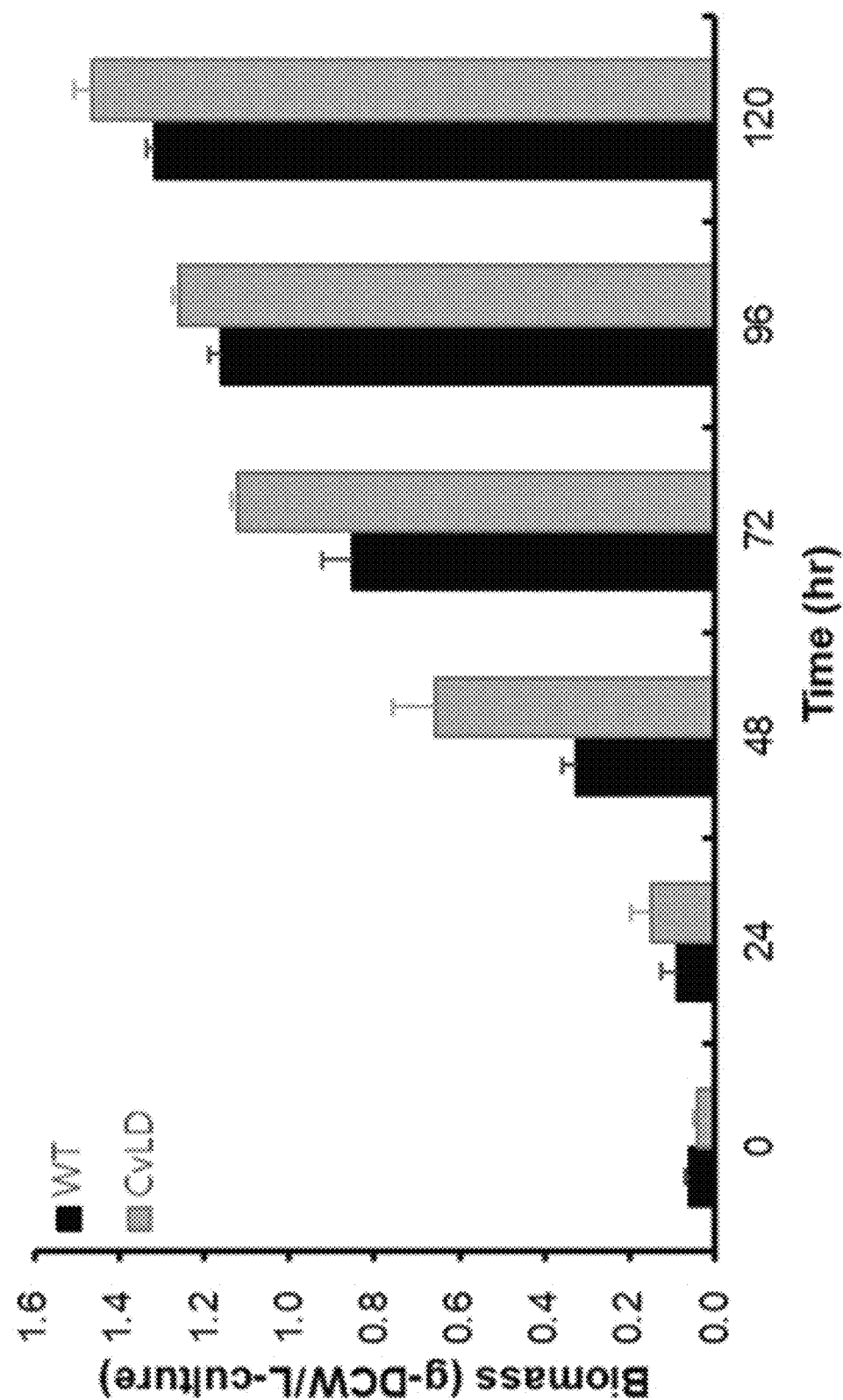
[Fig. 4C]

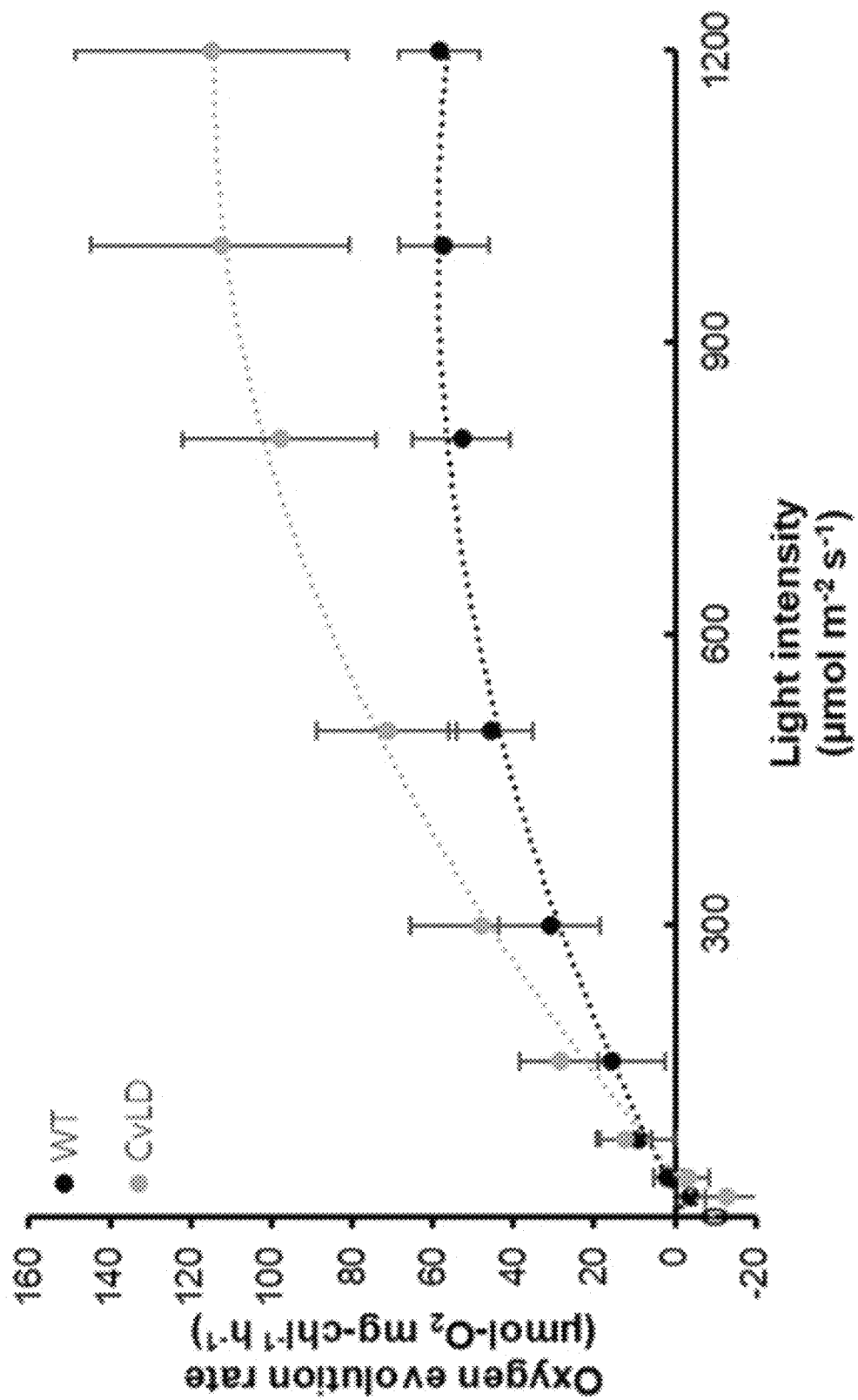
[Fig. 4D]

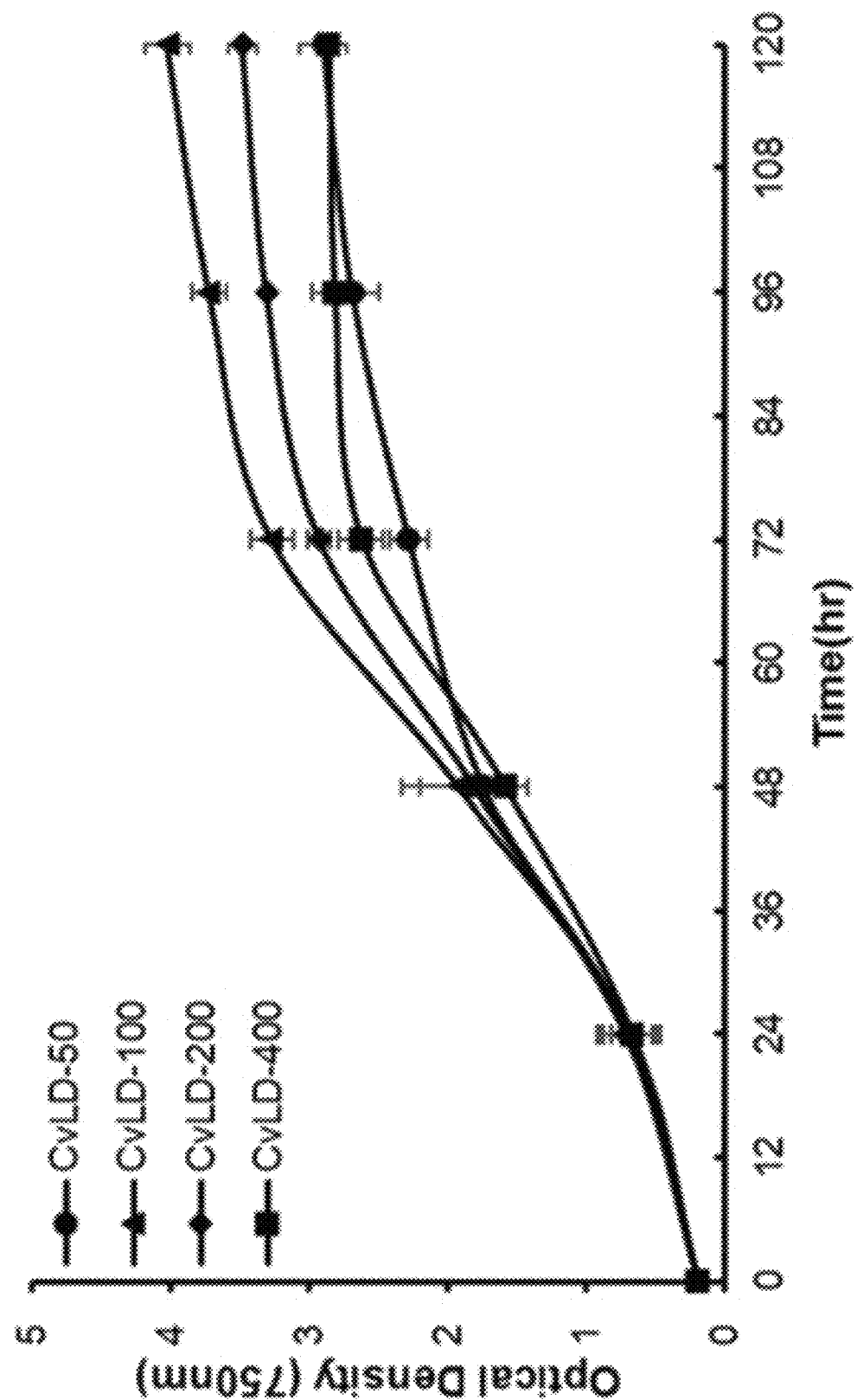
[Fig. 5A]

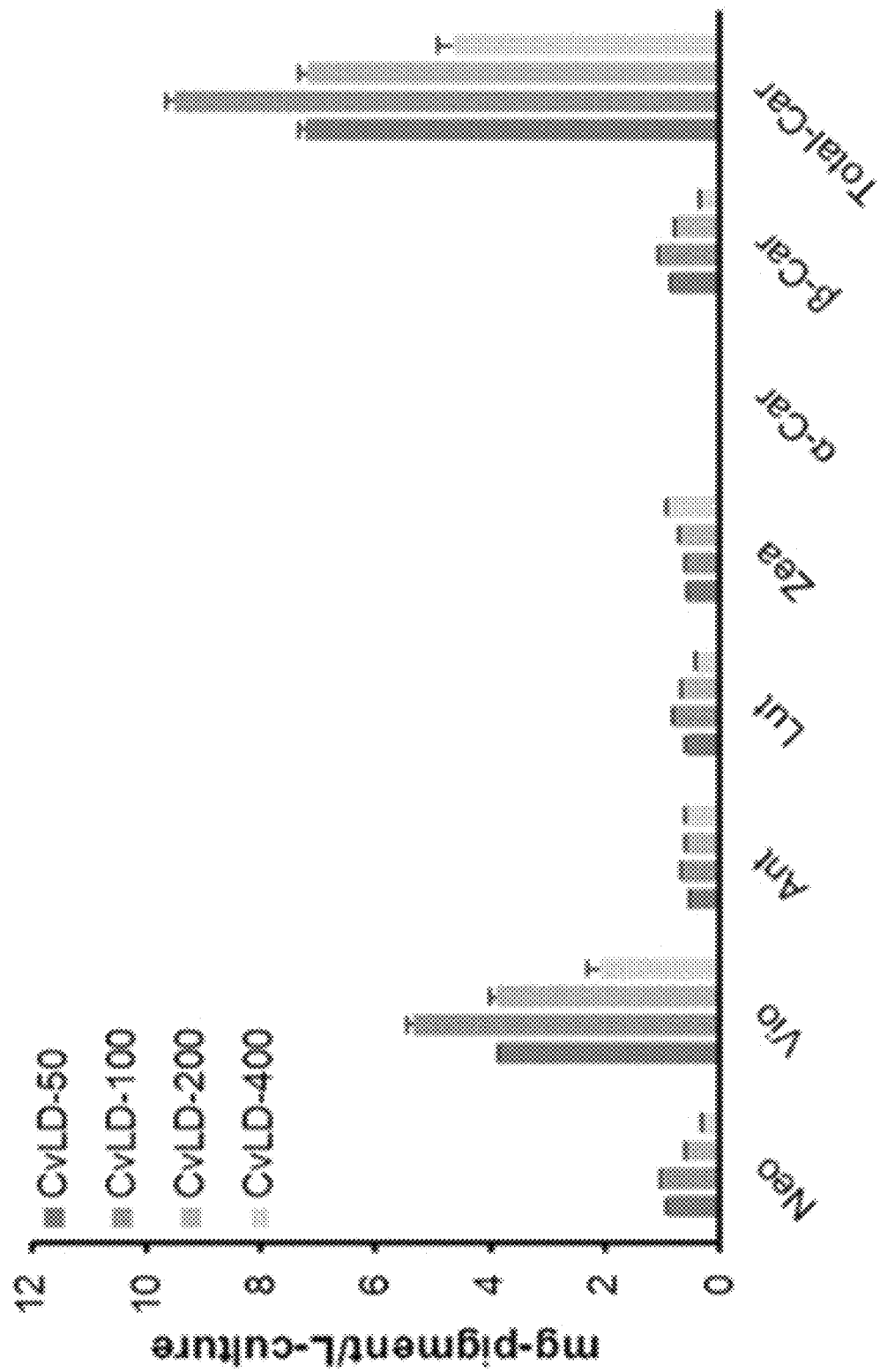
[Fig. 5B]

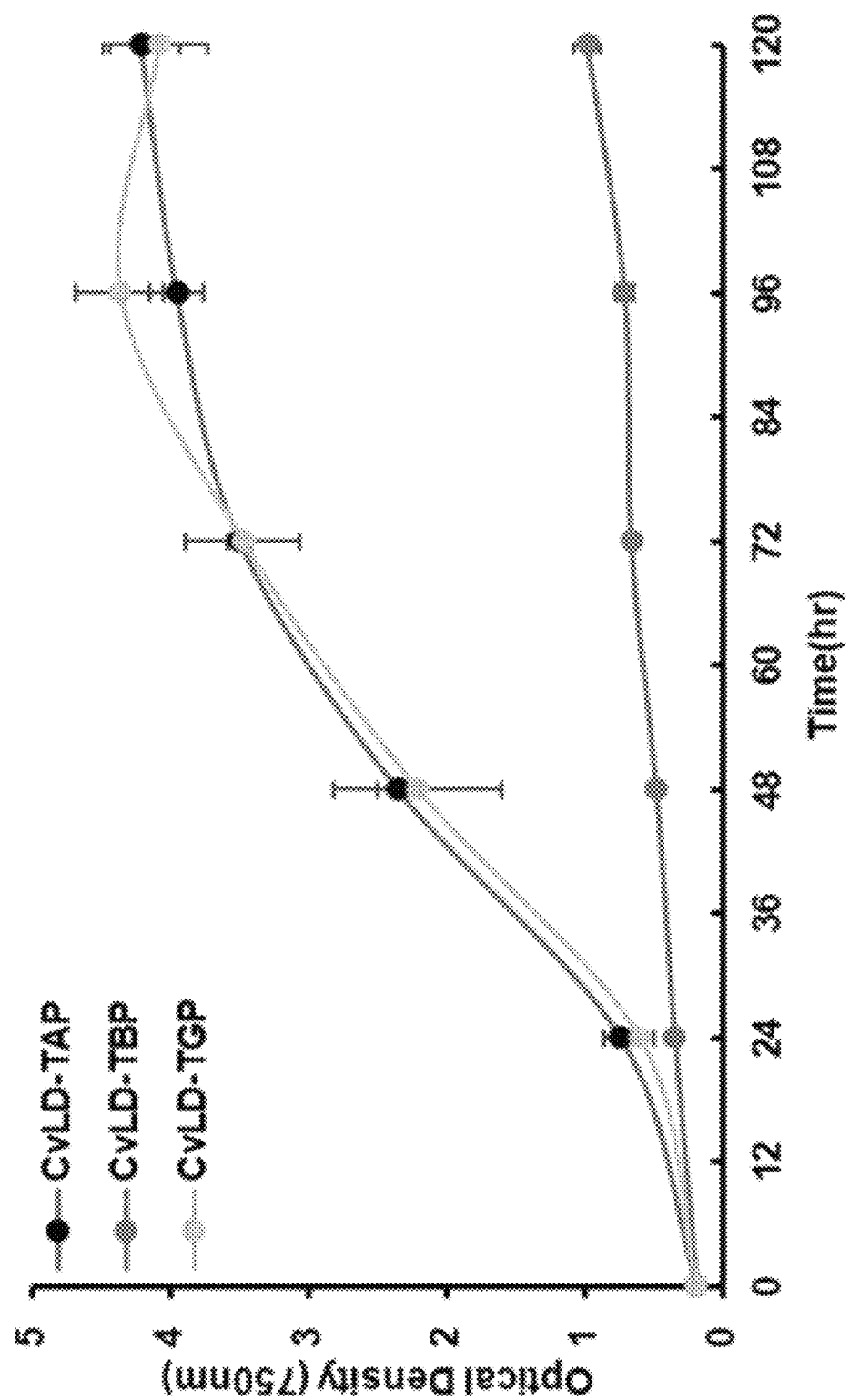
[Fig. 6A]

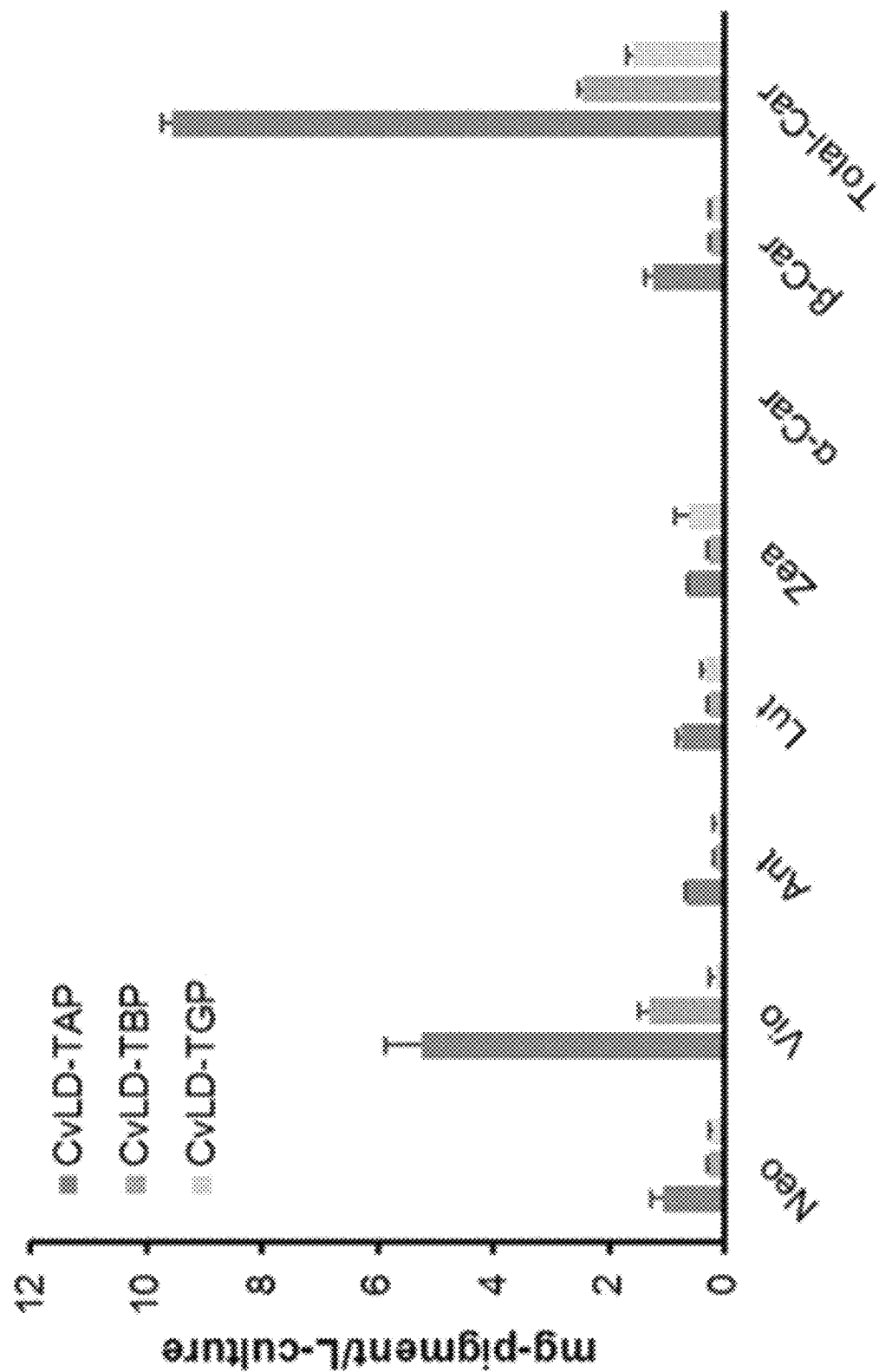
[Fig. 6B]

VIOLAXANTHIN-OVERPRODUCING STRAIN OF *CHLORELLA VULGARIS* AND THE METHOD FOR PRODUCING VIOLAXANTHIN USING THE SAME

CROSS-REFERENCE TO RELATED APPLICATION

This application claims priority to and the benefit of Korean Patent Application No. 2020-0014252, filed on Feb. 6, 2020, the disclosure of which is incorporated herein by reference in its entirety.

BACKGROUND

1. Field of the Invention

The present invention relates to a novel violaxanthin-overproducing *Chlorella vulgaris* strain and a method of producing violaxanthin therefrom, and more particularly, to a violaxanthin-overproducing *Chlorella vulgaris* mutant prepared by chemically inducing a mutation and a method of producing violaxanthin therefrom.

2. Discussion of Related Art

Microalgae are single-cell organisms known to have potential to produce a bioactive compound as well as having a high photosynthetic property and a high growth rate. The study on microalgae has mainly focused on the production of bio-oils, fatty acid nutrients (e.g., docosahexaenoic acid and eicosapentaenoic acid (EPA)) and carotenoid pigments, and recently, microalgae that produce expensive carotenoids such as astaxanthin, β-carotene, lutein and zeaxanthin are receiving considerable attention.

Carotenoids are isoprenoids that are considered natural pigments, and their specific colors range from yellow to red, and are present in many kinds of flowers, fruits and vegetables. Carotenoids consist of 40 carbon atoms and 8 isoprene units, and are synthesized in all photosynthetic organisms including cyanobacteria, algae and higher plants. Carotenoids are classified into two groups: carotenes, which are unsaturated hydrocarbons, and xanthophylls, which are oxidized carotenoids, and microalgae are mainly known to produce the xanthophyll family. Among these pigments, the most widely commercialized carotenoids produced from microalgae are astaxanthin, β-carotene, fucoxanthin and zeaxanthin. The microalgae-derived carotenoid pigments are widely used in pharmaceuticals (anti-cancer, anti-inflammatory, etc.) to nutritional supplements (antioxidants, etc.) and cosmetics (anti-aging, UV blocking, etc.). Particularly, in the global market, the demands for microalgae-derived carotenoids in animal feed, health functional foods and cosmetics are growing significantly.

In addition to the pigments described above, microalgae can produce other important carotenoids such as violaxanthin, neoxanthin and canthaxanthin. 5,6,5',6'-diepoxy-5,6,5',6'-tetrahydro-β,β-carotene-3,3'-diol (violaxanthin) is a natural xanthophyll pigment found in various plants and algae. This is a structure having 5,6-epoxy groups at both ends by zeaxanthin epoxidase using zeaxanthin as a substrate, and has a yellow color. It has been reported that violaxanthin has antioxidant activity like other carotenoids, and anti-inflammatory activity and antioxidant activity against human cancer cells. In addition, it is known that, under an acidic condition like the stomach, violaxanthin can be converted into auroxanthin, which is a very powerful antioxidant (J Agric Food Chem. 2016 Dec. 14; 64(49):9352-9355). Accordingly, if reliable productivity can be achieved through microalgae, the application of violaxanthin to potential pharmaceuticals and nutritional supplements is noteworthy.

However, despite the biological activity, violaxanthin is not continuously accumulated in a living body because it is interconverted with zeaxanthin in the xanthophyll cycle, and is used as a precursor of abscisic acid in higher plants and thus not highly maintained in content, compared to other carotenoid pigments. In addition, due to a characteristic of easily losing epoxy groups present at both ends, the production of violaxanthin is not easy. The productivity of violaxanthin from microalgae, which is currently reported, is maximum 0.38% in *Eustigmatos* cf. *polyphem*, and is approximately 0.05 to 0.17% based on dry weight in commercially available species (*Chlorella*, *Chlamidomonas*, *Dunaliella*, etc.). Therefore, it is necessary to develop a novel microalgae strain with an increased intracellular content of violaxanthin.

Meanwhile, *Chlorella vulgaris* is freshwater microalgae approved as a food ingredient, generally used as protein supplements or fish/animal feed, and can produce a carotenoid pigment due to being photosynthetic green microalgae. Despite the possibility of various applications, *Chlorella vulgaris* has been limited in its use since it is not easy to extract useful materials. Since *Chlorella vulgaris* is surrounded by the very rigid cell wall, no intracellular material is extracted through a material extraction method using a general extraction solvent. Until now, extraction methods applied to *Chlorella vulgaris* include vortexing, sonication, high pressure extraction and bead milling, but an optimized cell disruption method has not been developed, and it is known that the ultrasonic disruption method is most effective. Therefore, to effectively extract violaxanthin, which is a carotenoid pigment produced from *Chlorella vulgaris*, additional improvement in the conventional extraction method is needed.

SUMMARY OF THE INVENTION

As such, in order to improve low intracellular content and low intracellular pigment extraction yield, which are the main limitations in the production of violaxanthin of the prior art, the inventors developed a *Chlorella vulgaris* strain with a significantly improved violaxanthin content through a random chemical mutation, and established a method of more effectively extracting a pigment containing violaxanthin from the strain, and optimal culture conditions that can maximize the production of violaxanthin from the strain, and thus the present invention was completed.

Therefore, the present invention is directed to providing a violaxanthin-overproducing *Chlorella vulgaris* strain.

The present invention is also directed to providing a method of extracting a carotenoid pigment from the strain.

The present invention is also directed to providing a method of producing violaxanthin from the strain on a large scale.

However, technical problems to be solved in the present invention are not limited to the above-described problems, and other problems which are not described herein will be fully understood by those of ordinary skill in the art from the following descriptions.

To attain the purpose of the present invention, the present invention provides a violaxanthin-overproducing *Chlorella vulgaris* CvLD-01 strain (Accession No. KCTC 14091BP).

In one embodiment of the present invention, the strain may be derived from a *Chlorella vulgaris* UTEX395 strain.

In another embodiment of the present invention, the strain may have alanine (A), which is amino acid 336 of the lycopene epsilon cyclase gene (CvLCYE), substituted with valine (V).

In addition, the present invention provides a method of extracting a carotenoid pigment from the *Chlorella vulgaris* strain using glass bead-added sonication.

In one embodiment of the present invention, the extraction method may use methanol as a solvent.

In another embodiment of the present invention, the glass bead may have a diameter of 0.4 to 0.7 mm.

In addition, the present invention provides a method of producing violaxanthin on a large scale, which includes culturing the *Chlorella vulgaris* CvLD-01 strain.

In one embodiment of the present invention, the culture may be performed for 72 to 96 hours in a medium containing acetic acid as a carbon source under 100 μmol photon $m^{-2} s^{-1}$.

In addition, the present invention provides a composition for food or a food additive, which includes one or more selected from the group consisting of the *Chlorella vulgaris* CvLD-01 strain, a dry product thereof, a culture broth thereof and an extract thereof.

In addition, the present invention provides a composition for an antioxidant health functional food, which includes one or more selected from the group consisting of the *Chlorella vulgaris* CvLD-01 strain, a dry product thereof, a culture broth thereof and an extract thereof.

In addition, the present invention provides a cosmetic composition, which includes one or more selected from the group consisting of the *Chlorella vulgaris* CvLD-01 strain, a dry product thereof, a culture broth thereof and an extract thereof.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1B shows the result of comparatively analyzing pigment extraction efficiency by extracting each of chlorophyll-a (Chl-a) and chlorophyll-b (Chl-b) from a *Chlorella vulgaris* strain by each of the three extraction methods;

FIG. 2A shows the result of fluorescence analysis using IMAGING-PAM of observing and analyzing the phenotypes of the wild type and mutant strains of *Chlorella vulgaris* which are cultured in TAP media, and FIG. 2B shows the result of profiling various pigments produced in the strains through HPLC (WT: wild type strain, CvLD: mutant strain);

FIG. 3A shows a carotenoid biosynthesis pathway for the comparison results obtained by sequencing of lycopene epsilon cyclase (CvLCYE) and the analysis of a three-dimensional structure, FIG. 3B shows the result of aligning CvLCYE amino acid sequences of wild-type *Chlorella vulgaris* (*C. vulgaris*), other species including *Arabidopsis thaliana* and a mutant strain (*C. vulgaris* LD) according to the present invention (*A. thaliana*: SEQ ID NO: 5, *C. reinhardtii*: SEQ ID NO: 6, *C. variabilis*: SEQ ID NO: 7, *C. vulgaris*: SEQ ID NO: 8, *C. vulgaris* LD: SEQ ID NO: 9), FIG. 3C shows the result of comparatively analyzing expected 3D structures of CvLCYE using a SWISS-mode, and FIG. 3D shows the result of comparing CvLCYE mRNA expression levels in wild-type *Chlorella vulgaris* and the mutant strain (CvLD) according to the present invention;

FIG. 4A shows the results of analyzing the growth rates of wild-type *Chlorella vulgaris* and a mutant strain according to the present invention in flask culture, which shows the result of comparing a cell growth rate over time for each strain having a cell density of $1 \times 10^4$ cells/mL, FIG. 4B shows the result of comparing cell growth rates between the strains by measuring optical densities ($OD_{750}$), FIG. 4C shows the result of comparing a dry cell weight of each strain, and FIG. 4D shows the result of comparing an oxygen evolution rate according to light intensity in each strain;

FIG. 5A shows the result of culturing a mutant strain according to the present invention under various light intensity conditions, and analyzing a growth rate and carotenoid production, which shows a result of measuring an optical density ($OD_{750}$) and comparing a cell growth rate, and FIG. 5B shows production amounts of various pigments; and FIG. 6A shows the results of culturing mutant strains according to the present invention in media containing three different types of carbon sources and analyzing growth rates and carotenoid production, which shows a result of measuring optical densities and comparing growth rates of mutant strains cultured in media containing different carbon sources, and FIG. 6B shows a pigment production amount in each strain.

DETAILED DESCRIPTION OF EXEMPLARY EMBODIMENTS

Figure 1A:
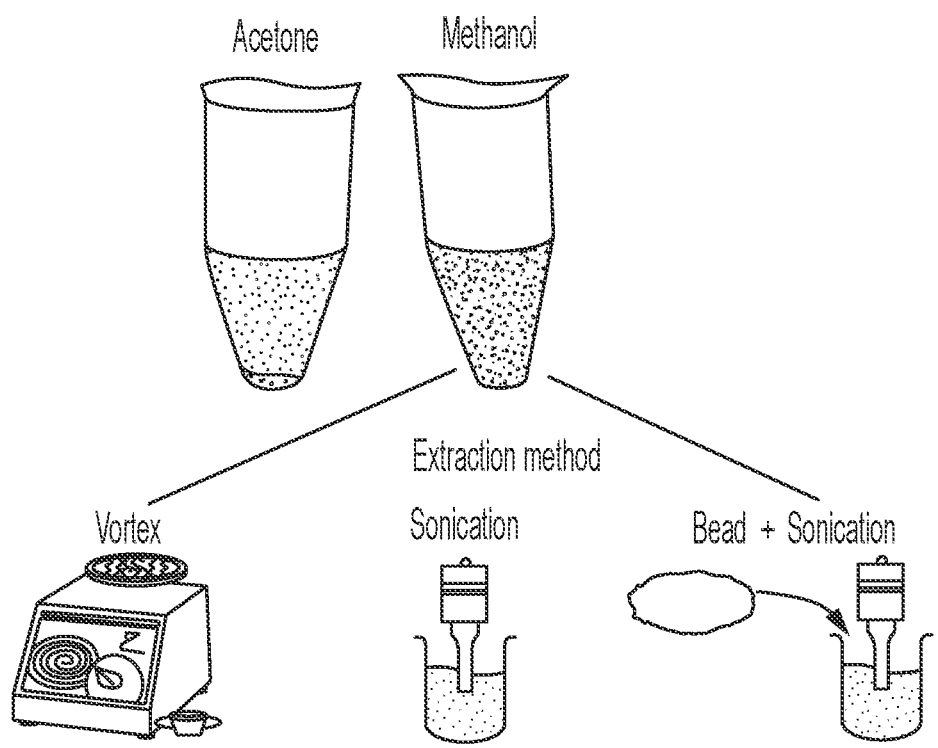
FIG. 1A shows the results of comparing methods of extracting carotenoid pigment from *Chlorella vulgaris*, shows vortexing with a vortex, sonication and glass bead-added sonication (Bead+Sonication) improved in the present invention.

The inventors have developed a *Chlorella vulgaris* mutant significantly improved in violaxanthin content by a random chemical mutation to improve the major limitations, such as low intracellular content and low intracellular pigment extraction yield, in violaxanthin production, and the strain was deposited with the Biological Resource Center of the Korea Research Institute of Bioscience and Biotechnology under Accession No. KCTC 14091BP. In addition, the inventors have established a method of effectively extracting a pigment containing violaxanthin in the strain and optimal culture conditions that can maximize violaxanthin production from the strain, and thus the present invention was completed.

Therefore, the present invention provides a violaxanthin overproducing *Chlorella vulgaris* CvLD-01 strain (Accession No. KCTC 14091BP).

In the present invention, *Chlorella vulgaris*, which is a strain used as a host strain for pigment production, is generally recognized as safe (GRAS) by US Food and Drug Administration and widely used as a component of health food and nutrient supplements.

In the present invention, a novel mutant strain that is able to accumulate violaxanthin was isolated using the *Chlorella vulgaris* strain, and a method of producing and isolating violaxanthin from the strain with the maximum efficiency was established.

In one embodiment of the present invention, mutations were randomly generated by treating a *Chlorella vulgaris* UTEX395 strain with EMS, a mutant exhibiting low fluorescence was selected first, and then a lutein-deficient mutant strain (CvLD) having excessive violaxanthin was finally selected through HPLC. As a result of HPLC, it was confirmed that antheraxanthin and zeaxanthin as well as violaxanthin also increased approximately 3 to 6-fold, and β-carotene increased 1.64-fold in the strain (see Example 3).

In another embodiment of the present invention, as a result of analyzing a gene mutated in the CvLD strain according to the present invention, it was confirmed that a CvLCYE gene involved in a carotenoid biosynthesis pathway is mutated (A336V). In addition, it was confirmed that a decrease in lutein in the CvLD strain is caused by the structural change of a protein of the gene by analyzing the 3D structure of the protein in the wild-type and CvLD strains (see Example 4).

In still another embodiment of the present invention, as a result of analyzing the growth rates of the wild type and CvLD in flask culture by various methods, it was confirmed that, overall, the cell growth of CvLD increases 1.2 to 1.4-fold, compared with the wild type. In addition, it was confirmed that the photosynthesis and respiration rates of the mutant strain are significantly higher than the wild type by an oxygen evolution rate, determining that such a difference affects the improvement in growth rate (see Example 5).

The results from the embodiments of the present invention through specific experiments prove that a violaxanthin-overproducing strain of Chlorella vulgaris according to the present invention is able to be used as a novel natural source for violaxanthin.

As described above, the Chlorella vulgaris strain according to the present invention has a property of excessively producing violaxanthin and lacks the ability to produce lutein. In addition, the production of one or more selected from the group consisting of antheraxanthin, zeaxanthin and β-carotene may be increased.

In addition, the growth rate of the Chlorella vulgaris strain according to the present invention may be increased 1.2 to 2-fold, preferably, 1.2 to 1.7-fold, more preferably, 1.2 to 1.5-fold, and still more preferably, 1.2 to 1.4-fold, compared to the wild-type strain.

In the present invention, the CvLCYE gene in which a mutation occurs in the Chlorella vulgaris strain is called a carotenoid psi-end group lyase (decyclizing), and is one of the enzymes involved in lycopene cyclization that coverts the carotenoid biosynthesis pathway into two metabolic branches, resulting in production of lutein by LCYE.

In another aspect of the present invention, the present invention provides a method of extracting a carotenoid pigment from the Chlorella vulgaris strain using glass bead-added sonication.

Specifically, in one embodiment of the present invention, an improved extraction method that can extract a carotenoid pigment from the Chlorella vulgaris strain with high efficiency was invented and its efficiency was analyzed, confirming that, when the glass bead-added sonication according to the present invention was used, the highest extraction efficiency is exhibited compared to when using vortexing and simple sonication (see Example 2).

In the present invention, sonication is one of the methods of disrupting cells to release an intracellular product, and a mechanical method of disrupting the cell wall and cell membrane of a cell due to a pressure change caused by generating a sound wave of 16 kHz or more. Here, the extraction efficiency of the carotenoid pigment from the strain may be further improved using a method improved by adding a 0.4 to 0.7, and preferably, 0.5 to 0.6-mm glass bead to apply a high shearing force and a high impact force may be further improved.

Here, as a solvent, methanol may be used, but the present invention is not limited thereto.

In still another aspect of the present invention, the present invention provides a method of producing violaxanthin on a large scale, which includes culturing the Chlorella vulgaris CvLD-01 strain.

In one embodiment of the present invention, to establish the optimal conditions of flask culture of a CvLD strain according to the present invention, the effect of light intensity and a carbon source was analyzed. First, it was confirmed that cell growth and violaxanthin production are not proportional to light intensity by measuring cell growth and carotenoid production of the mutant strain under various light intensity conditions, and the light intensity exhibiting the highest efficiency was confirmed (see Example 6). In addition, as a result of culturing the CvLD strain in a medium having different carbon sources and measuring cell growth and a carotenoid production rate, it can be seen that the strain uses acetic acid more effectively than glucose used. Further, after the CvLD strain was cultured under the optimal culture conditions deduced from the analysis, the production yield of violaxanthin was measured, resulting in reaching the highest yield of 0.41% (see Example 7).

Therefore, the culture for the mass production of violaxanthin may be performed for 72 to 96 hours in a medium containing acetic acid as a carbon source under 100 µmol photon $m^{-2}$ $s^{-1}$, but the present invention is not limited thereto.

In yet another aspect of the present invention, the present invention provides a composition for food or a food additive, which includes one or more selected form the group consisting of the Chlorella vulgaris CvLD-01 strain, a dry product thereof, a culture broth thereof and an extract thereof.

In yet another aspect of the present invention, the present invention provides a composition for health functional food, which includes one or more selected from the group consisting of the Chlorella vulgaris CvLD-01 strain, a dry product thereof, a culture broth thereof and an extract thereof.

The health functional food may exhibit an anticancer, antioxidant or anti-inflammatory effect, and preferably, an antioxidant effect, and may be used to improve a related disease or symptom.

The term "improvement" used herein refers to all types of actions that at least reduce parameters related to a condition to be treated, for example, a degree of a symptom, and the health functional food can be used before or after the onset of the corresponding disease, or simultaneously with or separately from a drug for treatment.

The term "health functional food composition" used herein includes one or more of a carrier, a diluent, an excipient and an additive, and is formulated into one selected from the group consisting of a tablet, a pill, a powder, a granule, a capsule and a liquid. Foods that can be added to the extract of the present invention may include various foods, powders, granules, tablets, capsules, syrups, beverages, gums, teas, vitamin complexes, and health functional foods. As an additive further included in the present invention, one or more types of ingredients selected from the group consisting of natural carbohydrates, sweeteners, nutrients, vitamins, minerals (electrolytes), flavoring agents (synthetic flavoring agents, natural flavoring agents, etc.), coloring agents, fillers, pectic acid and a salt thereof, alginic acid and a salt thereof, organic acids, protective colloid thickening agents, pH modifiers, stabilizers, preservatives, antioxidants, glycerin, alcohols, carbonating agents, and fruit flesh may be used. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, stevia extract (e.g., rebaudioside A, glycyrrhizin, etc.)] and synthetic sweeteners (saccharin, aspartame, etc.) may be advantageously used. In addition to the above ingredients, the composition according to the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, protective colloid thickening agents, pH modifiers, stabilizers, preservatives, glycerin, alcohols, or carbonating agents used in carbonated beverages. In addition, the composition according to the present invention may contain flesh for preparing natural fruit juices and vegetable juices. Such an ingredient may be used independently or in combination. Specific examples of the carriers, excipients, diluents and additives may include, but are not limited to, one or more selected from the group consisting of lactose, dextrose, sucrose, sorbitol, mannitol, erythritol, starch, acacia gum, calcium phosphate, alginate, gelatin, calcium phosphate, calcium silicate, microcrystalline cellulose, polyvinylpyrrolidone, cellulose, methyl cellulose, water, sugar syrup, methyl hydroxybenzoate, propyl hydroxybenzoate, talc, magnesium stearate, and mineral oil.

In a yet another aspect of the present invention, the present invention provides a cosmetic composition, which includes one or more selected from the group consisting of the *Chlorella vulgaris* CvLD-01 strain, a dry product thereof, a culture broth thereof and an extract thereof.

The cosmetic composition may have antioxidative, anti-aging or anti-inflammatory activity.

The cosmetic composition of the present invention may include the *Chlorella vulgaris* CvLD-01 strain, a dry product thereof, a culture broth thereof and an extract thereof, as well as components conventionally used in a cosmetic composition, for example, conventional adjuvants such as an antioxidant, a stabilizing agent, a solubilizer, vitamins, pigments and flavors, and a carrier.

In addition, the cosmetic composition of the present invention may include the *Chlorella vulgaris* CvLD-01 strain, a dry product thereof, a culture broth thereof and an extract thereof, and may be mixed with an organic UV blocking agent that has been conventionally used as long as it does not impair the skin protection effect. The organic sunscreen may be one or more selected from the group consisting of glyceryl PABA, drometrizole trisiloxane, drometrizole, digalloyl trioleate, disodium phenyl dibenzimidazole tetrasulfonate, diethylhexyl butamidotriazone, diethylamino hydroxybenzoyl hexylbenzoate, DEA-methoxycinnamate, a Lawson/dihydroxyacetone mixture, methylenebis-benzotriazolyltetramethylbutylphenol, 4-methylbenzylidene camphor, methyl anthranilate, benzophenone-3(oxybenzone), benzophenone-4, benzophenone-8 (dioxphebenzone), butyl methoxydibenzoylmethane, bis-ethylhexyloxyphenol methoxyphenyl triazine, cinoxate, ethyl dihydroxypropyl PABA, octocrylene, ethylhexyldimethyl PABA, ethylhexyl methoxycinnamate, ethylhexyl salicylate, ethylhexyl triazone, isoamyl-p-methoxycinnamate, polysilicon-15 (dimethicodiethylbenzal malonate), terephthalylidene dicamphor sulfonic acid and a salt thereof, TEA-salicylate and aminobenzoic acid (PABA).

Products that can contain the cosmetic composition of the present invention include, for example, cosmetics such as an astringent, a skin toner, a nourishing toner, various types of creams, essences, packs and foundations, cleansers, face washes, soaps, treatments, and tonics. Specific formulations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a pressed powder, a loose powder, and an eyeshadow.

According to an exemplary embodiment of the present invention, the content of the *Chlorella vulgaris* CvLD-01 strain, a dry product thereof, a culture broth thereof or an extract thereof may be 0.00001 to 30 wt %, preferably 0.5 to 20 wt %, and more preferably, 1.0 to 10 wt %, with respect to the total weight of the composition.

Hereinafter, to help in understanding the present invention, exemplary examples will be suggested. However, the following examples are merely provided to more easily understand the present invention, and not to limit the present invention.

EXAMPLES

Example 1. Experimental Materials and Methods 1-1. Strain Culture and Measurement of Growth Rate

*Chlorella vulgaris* UTEX395 (Culture Collection of the University of Texas at Austin, USA) was cultured in a Tris-acetate-phosphate (TAP) medium, and grown mixotrophically. To maintain wild-type and mutant strains, the strains were cultured in a filter-capped flask at 25° C. under 80 to 100 µmol photon $m^{-2}$ $s^{-1}$ (continuous) while shaking at 100 rpm. Afterward, an initial experiment for pigment and growth analyses was performed under the same conditions. The number of cells of the wild-type or mutant strain was counted using a Neubauer hemocytometer, and an optical density (OD) was measured through spectrophotometry at a wavelength of 750 nm. Meanwhile, to measure a biomass, 1 to 5 mL of cells were recovered by centrifugation at 3,200 rpm for 5 minutes, and a cell pellet was dried using a centrifugal vacuum concentrator (Biotron Inc., Bucheon-si, Gyeonggi-do, Korea). In addition, to compare growth rates, the initial cell concentration was $100 \times 10^4$ cells $mL^{-1}$, and initial $OD_{750}$=0.2 or 0.05 $gL^{-1}$. Specific cell growth was measured during the exponential phase, and the OD and biomass per cell were measured and calculated during the late log-stationary phase.

1-2. Optimization of Culture Conditions 1-2-1. Light Intensity

To determine the optimal light intensity for cell growth, cells were grown under four different irradiances: low light (45-50 µmol photon $m^{-2}$ $s^{-1}$); normal light (80-100 µmol photon $m^{-2}$ $s^{-1}$); medium light (200-250 µmol photon $m^{-2}$ $s^{-1}$); and high light (380-430 µmol photon $m^{-2}$ $s^{-1}$). Afterward, the cells were inoculated at $OD_{750}$=0.2, and grown for 5 days, followed by analyzing a pigment through high-performance liquid chromatography (HPLC).

1-2-2. Carbon Source

To verify the effect of a carbon source on pigment production, cells were incubated in each of three different media, that is, a TAP, Tris-bicarbonate-phosphate (TBP), medium and a Tris-glucose-phosphate (TGP) medium. An acetate medium (TAP) was used as a basal medium, and bicarbonate and glucose were cultured in TBP and TGP media at the same molar concentration (18.1 mM), respectively. Afterward, the cells were inoculated at $OD_{750}=0.2$, and incubated for 5 days, followed by analyzing a pigment through HPLC.

1-3. Preparation of Mutant Strain

Cells in the exponential phase were recovered and a mutation was induced using ethyl methanesulfonate (EMS). Specifically, approximately $1-2\times10^7$ cells were recovered in a 2 mL tube, and treated with 0.2-0.4 M EMS. The treated cells were cultured in a dark room for 2 hours, and washed with fresh TAP three times. Subsequently, the cells were resuspended in 500 µL of fresh TAP, and cultured overnight (6 to 18 hours) in the dark room using an orbital shaker. Afterward, the cells were plated in 5 solid TAP media, and when colonies were formed, a single colony was transferred to a fresh solid medium using a sterile toothpick for an additional experiment. Since a mutant strain having a high xanthophyll pigment level exhibited low fluorescence compared to the wild type, the mutant strain was screened based on the low fluorescence emission value using a fluorescence imaging system (IMAGING-PAM, Heinz-Walz, Effeltrich, Germany). Mutants exhibiting low fluorescence were additionally analyzed by HPLC, thereby selecting a xanthophyll-accumulated mutant strain.

1-4. In Vivo Fluorescence Analysis

Photosynthetic parameters of mixotrophically grown cells were measured in vivo in a TAP medium using a fluorescence imaging system (IMAGING-PAM, Heinz-Walz, Effeltrich, Germany). The cells in the exponential phase were filtered ($2.5\times10^7$ cells), transferred to a solid agar plate, and cultured in a dark room for 20 minutes. The cells were adapted to the dark, and a fluorescence dynamic curve was plotted with a saturated light pulse at 2,200 µmol photon $m^{-2}$ $s^{-1}$ and actinic light at 120 µmol photon $m^{-2}$ $s^{-1}$ by a 450-nm light-emitting diodes (LED) having a step width of 20 seconds.

1-5. Quantification of Xanthophyll Pigment and Chlorophyll

To quantify a pigment of a *Chlorella* strain, a modified extraction method was used. The xanthophyll pigment and chlorophyll of *C. vulgaris* were more effectively extracted using 100% ethanol than 90% acetone. In addition, pigment extraction efficiency was improved using ultrasonic extraction (Vibra-Cell, 130 Watts, 20 kHz) (Sonics, Newtown, Conn., USA). Finally, sonication (30 sec "on" and 5 sec "off", 5 min×60% amplitude) using 0.1 g of glass beads (0.5-0.6 mm) was additionally applied to the extraction method.

Subsequently, for pigment analysis, 0.2 mL of cells were recovered and centrifuged at 13,000 rpm for 1 minute, followed by extracting the xanthophyll pigment and chlorophyll through the above-described new extraction method; and sonication was performed by repeating "on" for 5 seconds and "off" for 5 seconds using a 6-mm probe at a 60% amplitude for 5 minutes. Afterward, the extracted xanthophyll pigment was analyzed using an HPLC system (LC-20AD, Shimadzu, Japan, Japan) equipped with a Waters Spherisorb S5 ODS1 column (4.6×250 mm; Waters, Milford, USA). Chlorophyll was analyzed by spectrophotometry. Chlorophyll a was measured at 665 nm, and chlorophyll b was measured at 652 nm. The concentrations of the xanthophyll pigment and chlorophylls were calibrated with a cell count or culture volume.

1-6. mRNA Expression of Lycopene Epsilon Cyclase and Proteomic Analysis of Amino Acid The inventors investigated a DNA sequence using an mRNA sequence (not shown) and aligned it with the entire genomic sequence (Accession No. PRJNA278897) to confirm a CvLCYE sequence. Additionally, mRNA expression of CvLCYE was confirmed by quantitative real-time polymerase chain reaction using TaKaRa PCR Thermal Cycler Dice (Takara, Shiga, Japan). More specifically, total RNA was extracted using a hybrid-R RNA prep kit with Trizol (GeneAll, Seoul, Korea), and cDNA was synthesized by reverse transcription using a random hexamer (EBT-1511, E1PIS BIO, Daejeon, Korea). To evaluate a CvLCYE mRNA expression level of in wild type and CvLD, CvLCYE was amplified with specific primers (forward: 5'-GTG TTT GGC ATG GAG CTG TTG TG-3' (SEQ ID NO: 1), reverse: 5'-CCA CGT GAG CAT CGC AAA GGT G-3' (SEQ ID NO: 2)), and 18s ribosome RNA was used as an internal control (forward: 5'-TAT GGG TGG TGG TGC ATG GC-3' (SEQ ID NO: 3), reverse: 5'-TGC CTC ATG CTT CCA TTG GCT-3' (SEQ ID NO: 4)). Raw data was analyzed by the ΔΔCt method using the software provided by the manufacturer.

The amino acid sequence of CvLCYE was determined by Sanger sequencing for cDNA (Macrogen, Seoul, Korea). To predict the CvLCYE structures of the wild-type and CvLCYE mutant strains, homology (comparative) modeling was performed, and to this end, a SWISS-model server was used. Conserved Archaeal protein (PDB: AOPI.1) was used as a template for constructing new CvLCYE. Finally, a predicted CvLCYE model was analyzed, and visualized using PyMOL 2.0 (http://www.pymol.org).

1-7. Measurement of Photosynthetic Activity

Cells were cultured in a TAP medium according to the method of Example 1-1, and the generation of oxygen in the wild-type and mutant strains was measured using a Clark-type oxygen electrode S1 (Hansatech, Norfolk, UK) illuminated by red LED (660 nm) at 25° C. The aliquot (1 mL) of a cell suspension ($4-5\times10^6$ cell $mL^{-1}$) was loaded in an electrode chamber, and to check whether oxygen evolution is not limited by the supply of carbon, 40 µL of 0.5 M $NaHCO_3$ was added before measurement. After the dark cycle, while increasing the light intensity (20, 40, 80, 160, 300, 500, 800, 1,000 and 1,200 µmol photon $m^{-2}$ $s^{-1}$), an oxygen evolution rate was measured and recorded for 2 minutes at each light intensity. In addition, after the oxygen evolution rate was measured at 1,200 µmol photon $m^{-2}$ $s^{-1}$, the cells were placed in a dark room for 5 minutes to measure oxygen respiration. The oxygen evolution rate was calibrated with a chlorophyll amount (mg) and time (h).

1-8. Statistical Analysis

Measurement of all growth rates and quantification of pigment analysis were performed at least three times, and statistical significance was verified by the Student's t-test, and when $p<0.05$, it is considered statistically significant.

Example 2. Improvement of Extraction Method for Extracting Carotenoid from *Chlorella vulgaris* and its Efficiency Analysis The inventors first tried to verify whether the improved extraction method described in Example 1-5 can more effectively extract the carotenoid pigment from *Chlorella vulgaris*. To this end, as shown in FIG. 1A, a methanol solvent was commonly used, and chlorophyll-a and chlorophyll-b were extracted by applying each of vortexing using a vortex, sonication and glass bead-added sonication (Bead+Sonication) improved in the present invention.

As a result, sonication showed higher pigment extraction efficiency than vortexing, and when the glass bead-added sonication according to the present invention was used, it can be seen that the highest extraction efficiency was exhibited, and as a result of quantification, the extraction efficiency was improved by 12%.

Example 3. Isolation of Vioxanthin-Accumulated Mutant Strain

A chemical mutagenic agent such as ethyl methanesulfonic acid (EMS) is known to be effective to produce algae mutants having high carotenoid contents. In addition, a xanthophyll mutant is able to be simply confirmed through fluorescence analysis. Therefore, in this example, a C. vulgaris UTEX395 strain in which a mutation was caused by EMS was screened through fluorescence analysis by IMAGING-PAM, and a mutant strain producing violaxanthin at a high level was confirmed through HPLC. Briefly, after EMS treatment, 1,600 colonies were randomly selected for phenotypic analysis, and then fluorescent analysis was performed to select mutants showing low fluorescence. HPLC was performed additionally on the 27 selected mutants, confirming one lutein-deficient mutant strain (hereinafter, CvLD) in which violaxanthin is abundantly present.

As shown in FIG. 2A, in the CvLD strain, fluorescence was reduced by approximately 50% in the same number of cells, compared to the wild-type strain (WT). However, unlike the obvious decrease in fluorescence, it was confirmed that the chlorophyll content was slightly reduced (wild type: 12.7±0.6 µg-Chl/$10^7$ cells, and CvLD: 11.1±0.8 µg-Chl/$10^7$ cells). In addition, according to HPLC, as shown in FIG. 2B and Table 1 below, compared to the wild-type strain, in CvLD, lutein (Lut) and α-carotene (α-car) were significantly reduced, but a β-branch pool of violaxanthin (Vio), antheraxanthin (Ant) and zeaxanthin (Zea) included in xanthophyll increased. More specifically, compared to the wild-type strain, in CvLD, lutein was reduced by 15.2%, whereas violaxanthin, antheraxanthin and zeaxanthin were increased 3.18-, 5.75- and 3.66-fold, respectively. In addition, α-carotene was reduced, whereas β-carotene was increased 1.64-fold.

TABLE 1

| Genotype | Carotenoid Pigments (µg/$10^7$ Cells) | | | | | | |
|---|---|---|---|---|---|---|---|
| | Neo | Vio | Ant | Lut | Zea | α-Car | β-Car |
| WT | 0.45 ± 0.04 | 0.44 ± 0.04 | 0.04 ± 0.01 | 1.71 ± 0.03 | 0.06 ± 0.00 | 0.06 ± 0.00 | 0.17 ± 0.01 |
| CvLD | 0.45 ± 0.02 | 1.40 ± 0.08 | 0.23 ± 0.02 | 0.26 ± 0.01 | 0.22 ± 0.01 | N.D. | 0.28 ± 0.01 |

Example 4. Confirmation of Gene Mutated in Carotenoid Biosynthesis Pathway

The inventors speculated that the increased accumulation of violaxanthin in CvLD is caused by a decrease in the α-branch of xanthophyll. According to the conventionally reported result, as shown in FIG. 3A, when CvLCYE was mutated in the genera Chlamydomonas, Ipomoea and Arabidopsis, the inhibition of α-branch synthesis and an increase in β-branch synthesis occurred simultaneously. Accordingly, to investigate the mutation of a carotenogenic gene in CvLD, the CvLCYE gene of C. vulgaris was intended to be identified.

Figure 3B:
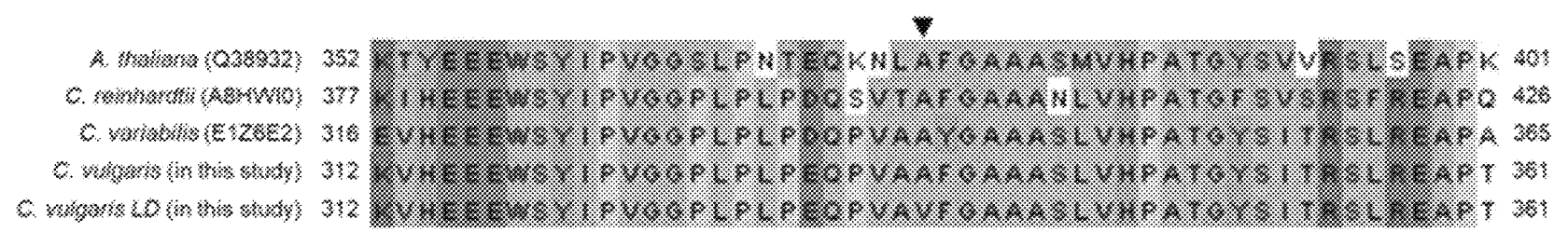

To this end, first, the encoded DNA sequence of CvLCYE of C. vulgaris was determined, confirming that, as shown in FIG. 3B, a single amino acid mutation (A336V) occurring in a highly-conserved region in LCYE of C. vulgaris, C. reinhardtii and A. thaliana. Subsequently, a homology model structure was formed using a SWISS-model server. As a result of structure analysis, as shown in FIG. 3C, compared to the wild-type strain, it was found that there is a structural difference around the mutant site, and structural changes in surrounding amino acids (indicated by a white arrow at a of FIG. 3C) were predicted. The structural change in this region seemed to be associated with the interaction of side chains between 336A and amino acids highlighted in b and c of FIG. 3C. As shown in FIG. 3D, since there is no significant difference in gene expression between the wild-type and CvLD, it was determined that a decrease in lutein in the CvLD mutant strain may be caused by the structural change in CvLCYE.

Example 5. Analysis of Growth Rates of Wild-Type and CvLD Strains in Flask Culture To compare the growth rates of the wild-type and CvLD strains, the number of cells, an optical density ($OD_{750}$ nm) and a dry cell weight were simultaneously measured. As shown in FIG. 4A, as a result of analyzing cell density, the maximum cell density of the wild-type (WT) strain was 3.17±0.14×$10^7$ cells m$L^{-1}$, whereas the maximum cell density of CvLD was 4.58±0.16×$10^7$ cells m$L^{-1}$, confirming that the maximum cell density of CvLD was 1.44-fold higher than that of the wild-type strain. In the WT strain and CvLD, the growth rates (da$y^{-1}$) based on the number of cells were 1.03±0.10 and 1.31±0.11, respectively. In addition, as a result of measurement of OD in FIG. 4B and a dry biomass (g/L) in FIG. 4C, similar results were also shown to the cell density results. Specifically, the OD difference between the wild-type and CvLD was shown to be 1.7 to 2.0-fold in the exponential phase, and 1.2-fold in the lag phase, and based on the dry weight of cells, it was confirmed that, in the exponential phase (24 to 72 hr), productivity was 0.38±0.03 g$L^{-1}$ da$y^{-1}$ in the case of the wild-type strain, and 0.49±0.02 g$L^{-1}$ da$y^{-1}$ in CvLD. Overall, it was found that the cell growth of CvLD was 1.2 to 1.4-fold higher than that of the wild-type strain.

Meanwhile, a change in photosynthesis efficiency is considered as the main cause frequently affecting microalgae growth. The inventors found that, through fluorescence analysis, the photosynthesis efficiency of CvLD can be higher than the wild-type strain. For more accurate comparison of photosynthesis efficiency, the oxygen evolution rates of the wild-type and CvLD were analyzed. As a result, as shown in FIG. 4D, as the light intensity increased in the range of 0 to 900 µmol photon $m^{-2}$ $s^{-1}$, the oxygen evolution rates increased. In addition, the half-saturation light intensities in the wild-type and CvLD were 308±71.3 and 322±36.4 µmol photon $m^{-2}$ $s^{-1}$, respectively.

As a result of analysis, since the oxygen evolution yield did not increase any more at 1,000 µmol photon $m^{-2}$ $s^{-1}$, the maximum oxygen evolution rate was measured at 1,000-1,200 µmol photon $m^{-2}$ $s^{-1}$. The maximum oxygen evolution rates were 59±9.8 µmol-$O_2$ mg-Ch$l^{-1}$ $h^{-1}$ (0.57±0.01 µmol-$O_2$ cel$l^{-7}$ $h^{-1}$) and 115±33.7 µmol-$O_2$ mg-Ch$l^{-1}$ $h^{-1}$ (1.03±0.30 µmol-$O_2$ cel$l^{-7}$ $h^{-1}$) in the wild-type and CvLD, respectively. In addition, as a result of measurement of respirations of the wild-type and CvLD in the dark, oxygen consumption rates after lights-out were 33±15.4 µmol-$O_2$ mg-Ch$l^{-1}$ $h^{-1}$ and 56±3.3 µmol-$O_2$ mg-Ch$l^{-1}$ $h^{-1}$ in the wild-type and CvLD, respectively. The oxygen evolution and consumption rates were calibrated with a chlorophyll content in a sample, and comprehensively, through the analysis results, it was confirmed that the photosynthesis and respiration rates of CvLD are significantly higher than those of the wild-type strain (p<0.05), and it was determined that such a difference probably causes the improved growth rate of CvLD.

Example 6. Analysis of Effect of Light Intensity on Cell Growth and Carotenoid Production The inventors measured cell growth and carotenoid production of the CvLD strain under four different light conditions (50, 100, 200 and 400 µmol photon $m^{-2}$ $s^{-1}$) to investigate the optimal culture conditions for violaxanthin production. As shown in FIG. 4D, oxygen evolution increased as the light intensity increased, the inventors assumed that the growth rate of CvLD increases with light intensity.

Therefore, as a result of the cell growth analysis of the CvLD strain, unexpectedly, as shown in FIG. 5A, the growth rate of CvLD in the range of 50 to 400 µmol photon $m^{-2}$ $s^{-1}$ was not proportional to light intensity. The maximum growth was 4.02 ($OD_{750}$) at 100 µmol photon $m^{-2}$ $s^{-1}$, and the cell growth was reduced at 200 µmol photon $m^{-2}$ $s^{-1}$. At 400 µmol photon $m^{-2}$ $s^{-1}$, the cell growth was reduced to the level shown at 50 µmol photon $m^{-2}$ $s^{-1}$. This result may be due to the light suppression effect caused by high light intensity. Accordingly, under the four light conditions which are the same as used above, various carotenoid concentrations produced by the CvLD strain were measured. As a result, as shown in FIG. 5B, it was confirmed that violaxanthin was abundantly present under the light condition, and its amount was dependent on light intensity.

As a result, it can be seen that carotenoid production shows a similar pattern to cell growth. The total carotenoid production in the CvLD strain reached the maximum level at 100 µmol photon $m^{-2}$ $s^{-1}$, and all carotenoid pigments were dramatically reduced at 400 µmol photon $m^{-2}$ $s^{-1}$. In addition, in terms of cell growth and carotenoid production, responses to various light intensities were similar to those in the wild-type strain.

Example 7. Analysis of Effect of Carbon Source on Cell Growth and Carotenoid Production Further, the inventors measured the cell growth and violaxanthin production of CvLD in various culture media according to the method described in Example 1-2-2 to analyze the effect of a carbon source on the violaxanthin production and investigate optimal conditions. Generally, C. vulgaris is known to well grow using glucose as a carbon source under heterotrophic and mixotrophic conditions. In this experiment, a common carbon source of green microalgae, acetic acid, was used, and a comparative culture experiment was performed to examine growth using acetic acid (TAP medium) and glucose (TGP medium) and pigment production. In addition, as an alternative to organic carbon, bicarbonate ($HCO_3^-$) was used (TBP medium) to simulate autotrophic culture.

As a result of culturing the CvLD strain in each medium and analyzing cell growth, as shown in FIG. 6A, the maximum cell density of CvLD was similar to that in the TAP and TGP media, the maximum growth reached 4.2 ($OD_{750}$) in the TAP medium, and 4.3 ($OD_{750}$) in the TGP medium. However, the initial cell growth period of CvLD extended in the TGP medium, and the growth was then drastically reduced after the lag phase. Therefore, from the result, it was confirmed that CvLD uses acetic acid more effectively than glucose. In addition, when the bicarbonate (inorganic carbon) is a carbon source, the cell growth of CvLD was remarkably low. Moreover, in an air injection experiment using a TAP medium, additional air supply seemed to inhibit cell growth (data is not shown).

As a result of carotenoid production analysis, as shown in FIG. 6B, acetic acid was shown to be most effectively used by CvLD. When glucose is supplied as a carbon source, carotenoid pigment and chlorophyll were reduced by less than 30%, compared to the TAP medium.

Finally, the inventors examined a violaxanthin production yield of the CVLD strain under the optimal conditions for the highest growth and pigment production as described above. As a result, as shown in Table 2 below, in flask culture, violaxanthin production reached 0.41% (3.7±0.45 mg/g-DCW) in the TAP medium at 100 µmol photon $m^{-2}$ $s^{-1}$. Accordingly, it was experimentally confirmed that CvLD can be effectively used by substituting a conventional source as a source that produces natural violaxanthin in a high yield.

TABLE 2

| Pigment production | Pigment amount in CvLD | | | | | | |
| --- | --- | --- | --- | --- | --- | --- | --- |
| | Neo | Vio | Ant | Lut | Zea | α-Car | β-Car |
| mg/L-culture | 1.05 ± 0.22 | 5.23 ± 0.64 | 0.64 ± 0.04 | 0.76 ± 0.06 | 0.63 ± 0.03 | N.D. | 1.24 ± 0.13 |
| mg/g-DCW | 0.74 ± 0.16 | 3.70 ± 0.45 | 0.45 ± 0.03 | 0.54 ± 0.04 | 0.44 ± 0.02 | N.D. | 0.88 ± 0.09 |

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

Microorganism: *Chlorella vulgaris* CvLD-01 Strain
Name of Depository Authority: Biological Resource Center of Korea Research Institute of Bioscience and Biotechnology
Address of depository: Biological Resource Center of Korea Research Institute of Bioscience and Biotechnology, 181 Ipsin-gil, Jeongeup-si, Jeollabuk-do 56212, Korea
Accession No.: KCTC14091BP
Deposition Date: Dec. 20, 2019

What is claimed is:

1. A violaxanthin-overproducing *Chlorella vulgaris* CvLD-01 strain (Accession No. KCTC 14091BP).

2. The strain of claim 1, wherein the strain is derived from a *Chlorella vulgaris* UTEX395 strain (Accession No. KCTC 14091BP).

3. The strain of claim 1, wherein the strain has alanine (A), which is amino acid 336 of the lycopene epsilon cyclase (CvLCYE) gene, substituted with valine (V) (Accession No. KCTC 14091BP).

4. A method of extracting carotenoid pigment from the *Chlorella vulgaris* strain of claim 1 using glass bead-added sonication.

5. The method of claim 4, wherein the extraction method uses methanol as a solvent.

6. The method of claim 4, wherein the glass bead has a diameter of 0.4 to 0.7 mm.

7. A method of producing violaxanthin on a large scale, which comprises culturing the *Chlorella vulgaris* CvLD-01 strain of claim 1.

8. The method of claim 7, wherein the culturing is performed for 72 to 96 hours in a medium containing acetic acid as a carbon source under 100 μmol photon $m^{-2}$ $s^{-1}$.

9. A composition for food or a food additive, comprising one or more selected from the group consisting of the *Chlorella vulgaris* CvLD-01 strain of claim 1, a dry product thereof, a culture broth thereof and an extract thereof.

10. An antioxidant method, comprising:
   injecting a composition comprising one or more selected from the group consisting of the *Chlorella vulgaris* CvLD-01 strain of claim 1, a dry product thereof, a culture broth thereof and an extract thereof into a subject.

11. A cosmetic composition, comprising one or more selected from the group consisting of the *Chlorella vulgaris* CvLD-01 strain of claim 1, a dry product thereof, a culture broth thereof and an extract thereof.

\* \* \* \* \*

SEQUENCE LISTING

<160> NUMBER OF SEQ ID NOS: 9

<210> SEQ ID NO 1
<211> LENGTH: 23
<212> TYPE: DNA

```
<213> ORGANISM: Artificial Sequence
<220> FEATURE:
<223> OTHER INFORMATION: CvLCYE_Forward

<400> SEQUENCE: 1
gtgtttggca tggagctgtt gtg                                              23

<210> SEQ ID NO 2
<211> LENGTH: 22
<212> TYPE: DNA
<213> ORGANISM: Artificial Sequence
<220> FEATURE:
<223> OTHER INFORMATION: CvLCYE_Reverse

<400> SEQUENCE: 2
ccacgtgagc atcgcaaagg tg                                               22

<210> SEQ ID NO 3
<211> LENGTH: 20
<212> TYPE: DNA
<213> ORGANISM: Artificial Sequence
<220> FEATURE:
<223> OTHER INFORMATION: 18s rRNA_Forward

<400> SEQUENCE: 3
tatgggtggt ggtgcatggc                                                  20

<210> SEQ ID NO 4
<211> LENGTH: 21
<212> TYPE: DNA
<213> ORGANISM: Artificial Sequence
<220> FEATURE:
<223> OTHER INFORMATION: 18s rRNA_Reverse

<400> SEQUENCE: 4
tgcctcatgc ttccattggc t                                                21

<210> SEQ ID NO 5
<211> LENGTH: 50
<212> TYPE: PRT
<213> ORGANISM: A. thaliana

<400> SEQUENCE: 5

Lys Thr Tyr Glu Glu Glu Trp Ser Tyr Ile Pro Val Gly Gly Ser Leu
1               5                   10                  15

Pro Asn Thr Glu Gln Lys Asn Leu Ala Phe Gly Ala Ala Ala Ser Met
            20                  25                  30

Val His Pro Ala Thr Gly Tyr Ser Val Val Arg Ser Leu Ser Glu Ala
        35                  40                  45

Pro Lys
    50

<210> SEQ ID NO 6
<211> LENGTH: 50
<212> TYPE: PRT
<213> ORGANISM: C. reinhardtii

<400> SEQUENCE: 6

Lys Ile His Glu Glu Glu Trp Ser Tyr Ile Pro Val Gly Gly Pro Leu
1               5                   10                  15

Pro Leu Pro Asp Gln Ser Val Thr Ala Phe Gly Ala Ala Ala Asn Leu
            20                  25                  30

Val His Pro Ala Thr Gly Phe Ser Val Ser Arg Ser Phe Arg Glu Ala
```

```
                    35                  40                  45

Pro Gln
    50

<210> SEQ ID NO 7
<211> LENGTH: 50
<212> TYPE: PRT
<213> ORGANISM: C. variabilis

<400> SEQUENCE: 7

Glu Val His Glu Glu Glu Trp Ser Tyr Ile Pro Val Gly Gly Pro Leu
1               5                   10                  15

Pro Leu Pro Asp Gln Pro Val Ala Ala Tyr Gly Ala Ala Ala Ser Leu
            20                  25                  30

Val His Pro Ala Thr Gly Tyr Ser Ile Thr Arg Ser Leu Arg Glu Ala
        35                  40                  45

Pro Ala
    50

<210> SEQ ID NO 8
<211> LENGTH: 50
<212> TYPE: PRT
<213> ORGANISM: C. vulgaris

<400> SEQUENCE: 8

Lys Val His Glu Glu Glu Trp Ser Tyr Ile Pro Val Gly Gly Pro Leu
1               5                   10                  15

Pro Leu Pro Glu Gln Pro Val Ala Ala Phe Gly Ala Ala Ala Ser Leu
            20                  25                  30

Val His Pro Ala Thr Gly Tyr Ser Ile Thr Arg Ser Leu Arg Glu Ala
        35                  40                  45

Pro Thr
    50

<210> SEQ ID NO 9
<211> LENGTH: 50
<212> TYPE: PRT
<213> ORGANISM: C.vulgaris LD

<400> SEQUENCE: 9

Lys Val His Glu Glu Glu Trp Ser Tyr Ile Pro Val Gly Gly Pro Leu
1               5                   10                  15

Pro Leu Pro Glu Gln Pro Val Ala Val Phe Gly Ala Ala Ala Ser Leu
            20                  25                  30

Val His Pro Ala Thr Gly Tyr Ser Ile Thr Arg Ser Leu Arg Glu Ala
        35                  40                  45

Pro Thr
    50
```